United States Patent
Jacobsen et al.

(10) Patent No.: US 11,535,600 B2
(45) Date of Patent: Dec. 27, 2022

(54) PRODRUGS OF 4-((1R,3S)-6-CHLORO-3-PHENYL-2,3-DIHYDRO-1H-INDEN-1-YL)-1,2,2-TRIMETHYLPIPERAZINE AND 4-((1R,3S)-6-CHLORO-3-(PHENYL-D₅)-2,3-DIHYDRO-1H-INDEN-1-YL)-2,2-DIMETHYL-1-(METHYL-D₃)PIPERAZINE

(71) Applicant: H. Lundbeck A/S, Valby (DK)

(72) Inventors: Mikkel Fog Jacobsen, Valby (DK); Morten Jørgensen, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 17/297,717

(22) PCT Filed: Nov. 27, 2019

(86) PCT No.: PCT/EP2019/082715
§ 371 (c)(1),
(2) Date: May 27, 2021

(87) PCT Pub. No.: WO2020/114853
PCT Pub. Date: Jun. 11, 2020

(65) Prior Publication Data
US 2022/0033367 A1 Feb. 3, 2022

(30) Foreign Application Priority Data

Dec. 3, 2018 (DK) .............................. PA201800947

(51) Int. Cl.
*C07D 295/03* (2006.01)
*C07D 295/037* (2006.01)

(52) U.S. Cl.
CPC ................................ *C07D 295/037* (2013.01)

(58) Field of Classification Search
CPC .................................................. C07D 295/037
See application file for complete search history.

(56) References Cited

U.S. PATENT DOCUMENTS

| | | |
|---|---|---|
| 4,684,650 A | 8/1987 | Bogeso |
| 5,807,855 A | 9/1998 | Bogeso et al. |

(Continued)

FOREIGN PATENT DOCUMENTS

| | | | |
|---|---|---|---|
| CN | 102020522 A | 4/2011 | |
| EP | 0638073 B1 | 2/1995 | |

(Continued)

OTHER PUBLICATIONS

Roland, James. Schizophrenia:No cure yet, but symptoms may be managed [online] May 3, 2021; retrieved on Feb. 26, 2022, URL; https://www.healthline.com/health/schizophrenia/can-schizophrenia-be-cured.*

(Continued)

*Primary Examiner* — Shawquia Jackson
(74) *Attorney, Agent, or Firm* — Wolf, Greenfield & Sacks, P.C.

(57) ABSTRACT

The present invention relates to prodrugs of 4-((1R,3S)-6-chloro-3-phenyl-2,3-dihydro-1H-inden-1-yl)-1,2,2-trimethylpiperazine in the form of 1a and 1b; and 4-((1R,3S)-6-chloro-3-(phenyl-d₅)-2,3-dihydro-1H-inden-1-yl)-2,2-dimethyl-1-(methyl-d₃)piperazine in the form of 2a and 2b, wherein X—is a counter ion, or pharmaceutically acceptable salts thereof. The present invention also provides pharmaceutical compositions comprising prodrugs, or pharmaceutically acceptable salts thereof, of the invention.

(I)

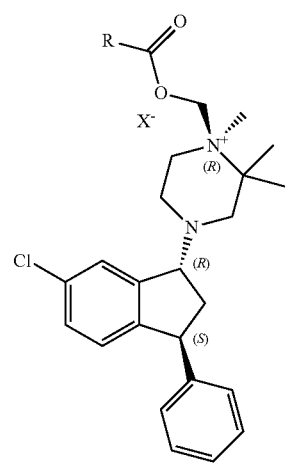

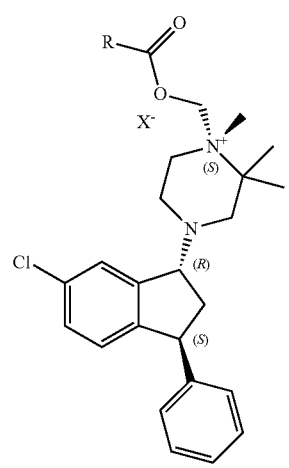

(Continued)

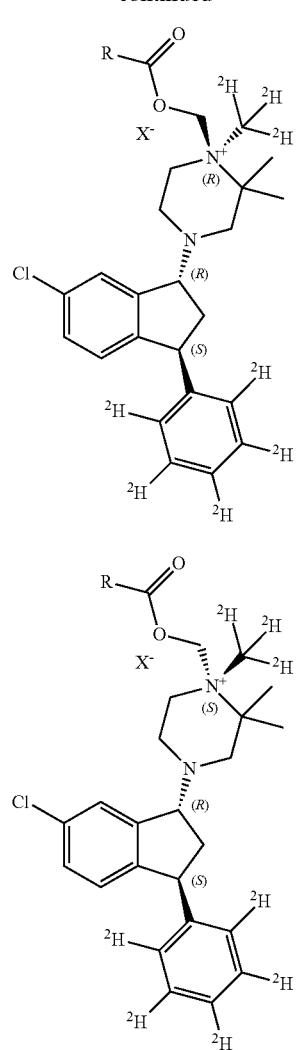

15 Claims, No Drawings

(56) References Cited

U.S. PATENT DOCUMENTS

| | | | |
|---|---|---|---|
| 6,221,335 | B1 | 4/2001 | Foster |
| 7,456,317 | B2 | 11/2008 | Gant et al. |
| 7,528,131 | B2 | 5/2009 | Persichetti et al. |
| 7,648,991 | B2 | 1/2010 | Bang-Andersen et al. |
| 7,678,914 | B2 | 3/2010 | Tung |
| 7,767,683 | B2 | 8/2010 | Lopez de Diego et al. |
| 7,772,240 | B2 | 8/2010 | Bang-Andersen et al. |
| 7,863,274 | B2 | 1/2011 | Tung |
| 8,076,342 | B2 | 12/2011 | Lopez de Diego et al. |
| 8,278,460 | B2 | 10/2012 | Liu et al. |
| 2008/0269248 | A1 | 10/2008 | Nielsen et al. |
| 2009/0062303 | A1 | 3/2009 | Czarnik |
| 2010/0069676 | A1 | 3/2010 | Dahl et al. |
| 2011/0178094 | A1 | 7/2011 | Holm et al. |
| 2011/0207744 | A1 | 8/2011 | Olsen et al. |
| 2012/0214991 | A1 | 8/2012 | Heo et al. |

FOREIGN PATENT DOCUMENTS

| | | |
|---|---|---|
| EP | 0988863 A2 | 3/2000 |
| EP | 1997479 A1 | 12/2008 |
| EP | 2639216 A1 | 9/2013 |
| EP | 3135656 A1 | 3/2017 |
| RU | 2366654 C2 | 9/2009 |
| WO | WO 1986/003488 A1 | 6/1986 |
| WO | WO 1992/010192 A1 | 6/1992 |
| WO | WO 1993/022293 A1 | 11/1993 |
| WO | WO 1995/026325 A2 | 10/1995 |
| WO | WO 1999/015524 A1 | 4/1999 |
| WO | WO 2001/049649 A1 | 7/2001 |
| WO | WO 2005/016900 A1 | 2/2005 |
| WO | WO 2005/016901 A1 | 2/2005 |
| WO | WO 2005/121087 A1 | 12/2005 |
| WO | WO 2006/086984 A1 | 8/2006 |
| WO | WO 2007/016431 A2 | 2/2007 |
| WO | WO 2008/086158 A1 | 7/2008 |
| WO | WO 2008/128166 A1 | 10/2008 |
| WO | WO 2009/135495 A1 | 11/2009 |
| WO | WO 2010/050897 A1 | 5/2010 |
| WO | WO 2010/062656 A2 | 6/2010 |
| WO | WO 2011/003423 A1 | 1/2011 |
| WO | WO 2011/022682 A1 | 2/2011 |
| WO | WO 2011/059080 A1 | 5/2011 |
| WO | WO 2012/137225 A1 | 10/2012 |
| WO | WO 2012/176066 A1 | 12/2012 |
| WO | WO 2014/096151 A2 | 6/2014 |

OTHER PUBLICATIONS

International Search Report and Written Opinion for Application No. PCT/EP2019/082715, dated Feb. 25, 2020.

International Preliminary Report on Patentability for Application No. PCT/EP2019/082715, dated Jun. 17, 2021.

[No Author Listed], Psychosis—information prescription. NHS Choices. Oct. 22, 2013. Retrieved from www.nhs.uk. 12 pages.

[No Author Listed], Psychosis defintion. A.D.A.M. Medical Encyclopedia [Internet]. Atlanta, GA. 2013. 2 pages. Retrieved from www.ncbi.nlm.nih.gov/pubmedhealth/PMH0002520/?report=printable.

Balsara et al., Effect of drugs influencing central serotonergic mechanisms on haloperidol-induced catalepsy. Psychopharmacology (Berl). Mar. 29, 1979;62(1):67-9. doi: 10.1007/BF00426037.

Beaman, Relation between (Apparent) Second-Order Transition Temperature and Melting Point. Journal of Polymer Science. 1952;9(5):470-472.

Berge et al., Pharmaceutical salts. J Pharm Sci. Jan. 1977;66(1):1-19. doi: 10.1002/jps.2600660104.

Blake et al., Studies with deuterated drugs. J Pharm Sci. Mar. 1975;64(3):367-91. doi: 10.1002/jps.2600640306.

Bøgesø et al., 3-Phenyl-1-indanamines. Potential antidepressant activity and potent inhibition of dopamine, norepinephrine, and serotonin uptake. J Med Chem. Dec. 1985;28(12): 1817-28. doi: 10.1021/jm00150a012.

Bøgesø et al., Enhanced D1 affinity in a series of piperazine ring substituted 1-piperazino-3-arylindans with potential atypical antipsychotic activity. J Med Chem. Oct. 27, 1995;38(22):4380-92. doi: 10.1021/jm00022a004.

Bøgesø Drug Hunting—The Medicinal Chemistry of 1-Piperazino-3-Phenylindans and Related Compounds. Doctoral Thesis. Nov. 1998. 144 pages.

Buteau, Deuterated Drugs: Unexpectedly Nonobvious? J High Tech L. 2009;10:22-74.

Caira, Crystalline Polymorphism of Organic Compounds. Topics in Current Chemistry. 1998;198:163-204.

Carlsson, Antipsychotic drugs, neurotransmitters, and schizophrenia. Am J Psychiatry. Feb. 1978;135(2):165-73. doi: 10.1176/ajp.135.2.165.

Clark et al., A highly enantioselective conjugate reduction of 3-arylinden-1-ones using bakers' yeast for the preparation of (S)-3-arylindan-1-ones. Org Lett. Dec. 2, 1999;1(11):1839-42. doi: 10.1021/ol991111+.

(56) References Cited

OTHER PUBLICATIONS

Dengale et al., Recent advances in co-amorphous drug formulations. Adv Drug Deliv Rev. May 1, 2016;100:116-25. doi: 10.1016/j.addr.2015.12.009. Epub Jan. 21, 2016.
Eder, CEE-03-310 CeNeS pharmaceuticals. Curr Opin Investig Drugs. Feb. 2002;3(2):284-8.
Fisher et al., The complexities inherent in attempts to decrease drug clearance by blocking sites of CYP-mediated metabolism. Curr Opin Drug Discov Devel. Jan. 2006;9(1):101-9.
Foster, Deuterium isotope effects in the metabolism of drugs and xenobiotics implications for drug design. Advances in Drug Research. 1985; 14. 40 pages.
Fukuto et al., Determination of the mechanism of demethylenation of (methylenedioxy)phenyl compounds by cytochrome P450 using deuterium isotope effects. J Med Chem. Sep. 1991;34(9):2871-6. doi: 10.1021/jm00113a028.
Gant, Using deuterium in drug discovery: leaving the label in the drug. J Med Chem. May 8, 2014;57(9):3595-611. doi: 10.1021/jm4007998. Epub Dec. 2, 2013.
Geyer et al., Chapter 50: Animal models relevant to schizophrenia disorders. Neuropsychopharmacology: The Fifth Generation of Progress. 2002. 689-701.
Gleason et al., Blockade of phencyclidine-induced hyperlocomotion by olanzapine, clozapine and serotonin receptor subtype selective antagonists in mice. Psychopharmacology (Berl). Jan. 1997;129(1):79-84. doi: 10.1007/s002130050165.
Grohganz et al., Amorphous drugs and dosage forms. J Drug Del Sci Tech. 2013;23(4):403-408.
Hancock et al., Comparison of the mechanical properties of the crystalline and amorphous forms of a drug substance. Int J Pharm. Jul. 8, 2002;241(1):73-85. doi: 10.1016/s0378-5173(02)00133-3.
Harbeson et al., Chapter 24: Deuterium in Drug Discovery and Development. Annual Reports in Medicinal Chemistry. 2011;46:403-417.
Jackson et al., Dopamine receptor antagonists block amphetamine and phencyclidine-induced motor stimulation in rats. Pharmacol Biochem Behav. Jun. 1994;48(2):465-71. doi: 10.1016/0091-3057(94)90554-1.
Jentsch et al., The neuropsychopharmacology of phencyclidine: from NMDA receptor hypofunction to the dopamine hypothesis of schizophrenia. Neuropsychopharmacology. Mar. 1999;20(3):201-25. doi: 10.1016/S0893-133X(98)00060-8.
Kundu et al., Hydroacylation of 2-vinyl benzaldehyde systems: an efficient method for the synthesis of chiral 3-substituted indanones. J Am Chem Soc. Nov. 23, 2005;127(46):16042-3. doi: 10.1021/ja0564416.
Kushner et al., Pharmacological uses and perspectives of heavy water and deuterated compounds. Can J Physiol Pharmacol. Feb. 1999;77(2):79-88.
Laitinen et al., Emerging trends in the stabilization of amorphous drugs. Int J Pharm. Aug. 30, 2013;453(1):65-79. doi: 10.1016/j.ijpharm.2012.04.066. Epub Apr. 28, 2012.
Mamada et al., Pharmacokinetic equivalence of deuterium-labeled and unlabeled phenytoin. Drug Metab Dispos. Jul.-Aug. 1986;14(4):509-11.
Martin et al., Highly enantioselective transfer hydrogenation of alpha,beta-unsaturated ketones. J Am Chem Soc. Oct. 18, 2006;128(41):13368-9. doi: 10.1021/ja065708d.
Mayo Clinic Staff, Bipolar Disorder. Retrieved from www.mayoclinic.com. Jan. 18, 2012. Accessed on Oct. 22, 2013. 20 pages.
Mayo Clinic Staff, Schizophrenia. Retrieved from www.mayoclinic.com. Jan. 27, 2012. Accessed on Oct. 22, 2013. 10 pages.
Minatti et al., Synthesis of chiral 3-substituted indanones via an enantioselective reductive-heck reaction. J Org Chem. Nov. 23, 2007;72(24):9253-8. doi: 10.1021/jo701741y. Epub Oct. 30, 2007.
Morgan et al., Evaluation of stable isotope-labeled probes in the study of solvent pharmacokinetics in human subjects. Int Arch Occup Environ Health. 1993;65(1 Suppl):S139-42. doi: 10.1007/BF00381326.
Mutlib et al., The species-dependent metabolism of efavirenz produces a nephrotoxic glutathione conjugate in rats. Toxicol Appl Pharmacol. Nov. 15, 2000;169(1):102-13. doi: 10.1006/taap.2000.9055.
Mutlib, Application of stable isotope-labeled compounds in metabolism and in metabolism-mediated toxicity studies. Chem Res Toxicol. Sep. 2008;21(9):1672-89. doi: 10.1021/tx800139z. Epub Aug. 15, 2008.
Sato, Expanding range of application of deuterium. Special Lecture. Wako Organic Square No. 33, pp. 2-4. 13 pages. Sep. 2010.
Sax et al., Hawley's Condensed Chemical Dictionary. 11th Ed. 1987. p. 355.
Seeman, Dopamine Receptors and Psychosis. Sci Am Sci Med. Sep./Oct. 1995:28-37.
Shao et al., The kinetic isotope effect in the search for deuterated drugs. Drug News Perspect. Jul.-Aug. 2010;23(6):398-404. doi: 10.1358/dnp.2010.23.6.1426638.
Silverman, Chapter 7, Section 4: Pathways for Drug Dactivation and Elimination. 2004:415-427.
Simeone et al., Palladium on carbon as a precatalyst for the Suzuki-Miyuara cross-coupling of aryl chlorides. Tetrahedron. 2007;63(2007):12646-12654. Epub Oct. 6, 2007.
Streeter et al., Single-dose toxicokinetics of n-nitrosomethylethylamine and n-nitrosomethyl (2,2,2-trideuterioethyl)amine in the rat. Arch Toxicol. 1990;64(2):109-15. doi: 10.1007/BF01974395.
Takagi et al., Palladium-catalyzed cross-coupling reaction of bis(pinacolato)diboron with 1-alkenyl halides or triflates: convenient synthesis of unsymmetrical 1,3-dienes via the borylation-coupling sequence. J Am Chem Soc. Jul. 10, 2002;124(27):8001-6. doi: 10.1021/ja0202255.
Tuttle et al., Organocatalytic transfer hydrogenation of cyclic enones. J Am Chem Soc. Oct. 4, 2006;128(39):12662-3. doi: 10.1021/ja0653066.
Weiden, EPS profiles: the atypical antipsychotics are not all the same. J Psychiatr Pract. Jan. 2007;13(1):13-24. doi: 10.1097/00131746-200701000-00003.
Willner, Dopamine and depression: a review of recent evidence. I. Empirical studies. Brain Res. Dec. 1983;287(3):211-24. doi: 10.1016/0165-0173(83)90005-x.

* cited by examiner

PRODRUGS OF 4-((1R,3S)-6-CHLORO-3-PHENYL-2,3-DIHYDRO-1H-INDEN-1-YL)-1,2,2-TRIMETHYLPIPERAZINE AND 4-((1R,3S)-6-CHLORO-3-(PHENYL-D₅)-2,3-DIHYDRO-1H-INDEN-1-YL)-2,2-DIMETHYL-1-(METHYL-D₃)PIPERAZINE

CROSS REFERENCE TO RELATED APPLICATIONS

This Application is a National Stage filing under 35 U.S.C. 371 of International Patent Application No. PCT/EP2019/082715, filed Nov. 27, 2019, which claims priority to Denmark Application Number PA201800947, filed Dec. 3, 2018. The entire contents of these applications are incorporated herein by reference in their entirety.

FIELD OF THE INVENTION

The present invention relates to prodrugs of 4-((1R,3S)-6-chloro-3-phenyl-2,3-dihydro-1H-inden-1-yl)-1,2,2-trimethylpiperazine in the form of 1a and 1b; and 4-((1R,3S)-6-chloro-3-(phenyl-d₅)-2,3-dihydro-1H-inden-1-yl)-2,2-dimethyl-1-(methyl-d₃)piperazine in the form of 2a and 2b, wherein $X^-$ is a counter ion,

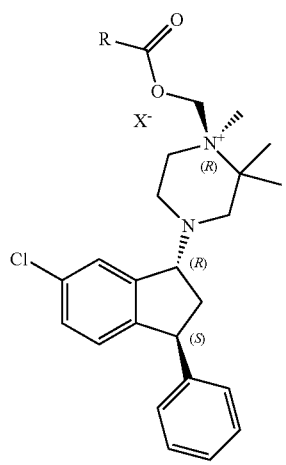

1a

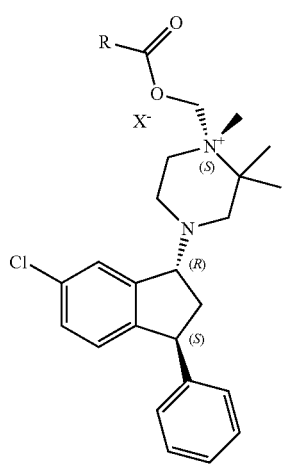

1b

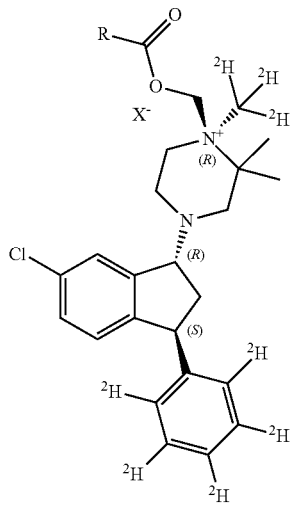

2a

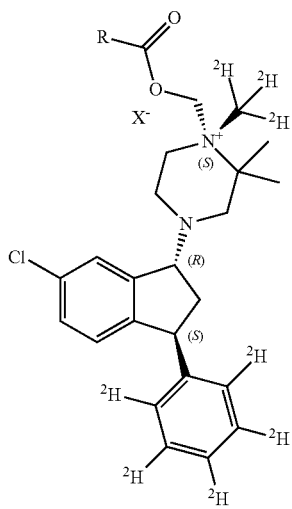

2b or pharmaceutically acceptable salts thereof.

The present invention also provides pharmaceutical compositions comprising prodrugs, or pharmaceutically acceptable salts thereof, of the invention.

BACKGROUND OF THE INVENTION

A group of trans isomers of 3-aryl-1-(1-piperazinyl)indanes substituted in the 2- and/or 3-position of the piperazine ring has been described in WO 93/22293 and in Klaus P. Bøgesø, Drug Hunting, the Medicinal Chemistry of 1-Piperazino-3-phenylindans and Related Compounds, 1998, *ISBN* 87-88085-10-4 (cf. e.g. compound 69 in table 3, p. 47 and in table 9A, p. 101). The compounds are described as having high affinity for dopamine $D_1$ and $D_2$ receptors and the 5-HT₂ receptor and are suggested to be useful for treatment of several diseases in the central nervous system, including schizophrenia.

Trans racemic 4-((6-chloro-3-phenyl-indan-1-yl)-1,2,2-trimethyl-piperazine may e.g. be synthesized analogously to the methods outlined in Bøgesø et al., J. Med. Chem., 1995, 38, p. 4380-4392 and in WO 93/22293. Manufacture of this compound by resolution of trans racemic 4-((6-chloro-3-phenyl-indan-1-yl)-1,2,2-trimethyl-piperazine has been described by Bøgesø et al. in J. Med. Chem., 1995, 38, p.

4380-4392, see table 5, compound (−)-38. The process described comprises the use of (+)-ditoluoyl tartaric acid for resolution in ethylacetate, and the compound is isolated as the fumarate salt. 4-((1R,3S)-6-chloro-3-phenyl-2,3-dihydro-1H-inden-1-yl)-1,2,2-trimethylpiperazine has subsequently been afforded the International Non-proprietary Name (INN) zicronapine by WHO. Salts of 4-((1R,3S)-6-chloro-3-phenyl-2,3-dihydro-1H-inden-1-yl)-1,2,2-trimethylpiperazine have been disclosed in WO 2005/016900, whereas later patent applications disclose alternative methods for the manufacture of 4-((1R,3S)-6-chloro-3-phenyl-2,3-dihydro-1H-inden-1-yl)-1,2,2-trimethylpiperazine (WO 2011/003423) and resolution of the same compound (WO 2012/093165). 4-((1R,3S)-6-chloro-3-(phenyl-$d_5$)-2,3-dihydro-1H-inden-1-yl)-2,2-dimethyl-1-(methyl-$d_3$)piperazine is deuterium ($^2$H) enriched 4-((1R,3S)-6-chloro-3-phenyl-2,3-dihydro-1H-inden-1-yl)-1,2,2-trimethylpiperazine in the positions indicated in 2a and 2b. 4-((1R,3S)-6-chloro-3-(phenyl-$d_5$)-2,3-dihydro-1H-inden-1-yl)-2,2-dimethyl-1-(methyl-$d_3$)piperazine has been disclosed in WO 2012/176066, which also discloses synthetic routes for obtaining 4-((1R,3S)-6-chloro-3-(phenyl-$d_5$)-2,3-dihydro-1H-inden-1-yl)-2,2-dimethyl-1-(methyl-$d_3$)piperazine.

WO 2014/096151 discloses a further synthetic route for obtaining 4-((1R,3S)-6-chloro-3-(phenyl-$d_5$)-2,3-dihydro-1H-inden-1-yl)-2,2-dimethyl-1-(methyl-$d_3$)piperazine via conversion of 3,5-dichloro-1-(phenyl-$d_5$)-indan.

The present invention provides prodrugs of 4-((1R,3S)-6-chloro-3-phenyl-2,3-dihydro-1H-inden-1-yl)-1,2,2-trimethylpiperazine and 4-((1R,3S)-6-chloro-3-(phenyl-$d_5$)-2,3-dihydro-1H-inden-1-yl)-2,2-dimethyl-1-(methyl-$d_3$) piperazine. The prodrugs of the present invention may e.g. improve uptake of 4-((1R,3S)-6-chloro-3-phenyl-2,3-dihydro-1H-inden-1-yl)-1,2,2-trimethylpiperazine and 4-((1R,3S)-6-chloro-3-(phenyl-$d_5$)-2,3-dihydro-1H-inden-1-yl)-2,2-dimethyl-1-(methyl-$d_3$)piperazine, delay the release of 4-((1R,3S)-6-chloro-3-phenyl-2,3-dihydro-1H-inden-1-yl)-1,2,2-trimethylpiperazine and 4-((1R,3S)-6-chloro-3-(phenyl-$d_5$)-2,3-dihydro-1H-inden-1-yl)-2,2-dimethyl-1-(methyl-$d_3$)piperazine, or lower the level of possible adverse events.

SUMMARY OF THE INVENTION

The invention provides compounds that are prodrugs as shown below (1a and 1b; 2a and 2b):

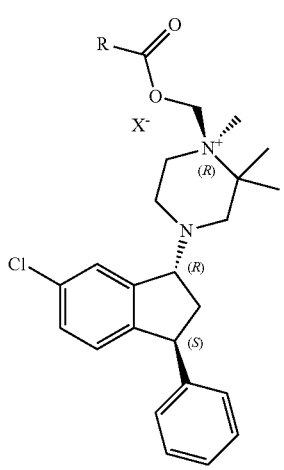

1a

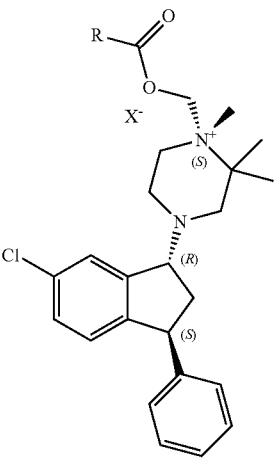

1b

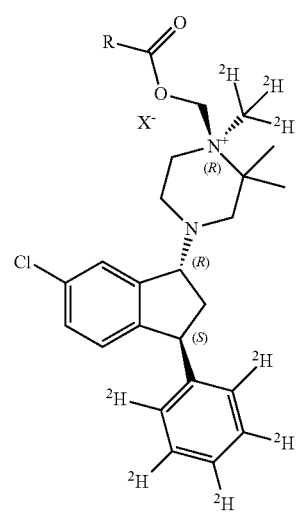

2a

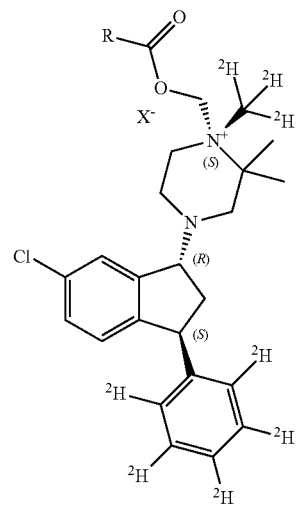

2b and pharmaceutically acceptable salts thereof.

1a and 2a are R-configured at the chiral nitrogen atom, while 1b and 2b are S-configured at the chiral nitrogen atom.

In one embodiment, the present invention provides a prodrug as defined above or a pharmaceutically acceptable salt thereof for use in therapy.

In one embodiment, the invention provides a pharmaceutical composition comprising a prodrug of the invention as defined above or a pharmaceutically acceptable salt thereof and one or more pharmaceutically acceptable excipients.

In one embodiment, the present invention provides a prodrug as defined above or a pharmaceutically acceptable salt thereof for use in a method for the treatment of a CNS disease.

In one embodiment, the invention provides the use of a prodrug as defined above or a pharmaceutically acceptable salt thereof for use in the manufacture of a medicament for the treatment of a CNS disease.

In one embodiment, the present invention provides a method for the treatment of a CNS disease, the method comprising the administration of a therapeutically effective amount of a prodrug as defined above or a pharmaceutically acceptable salt thereof to a patient in need thereof.

DETAILED DESCRIPTION OF THE INVENTION

The invention provides compounds that are prodrugs as shown below (1a and 1b; 2a and 2b):

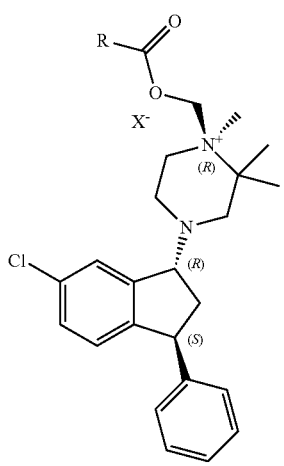

1a

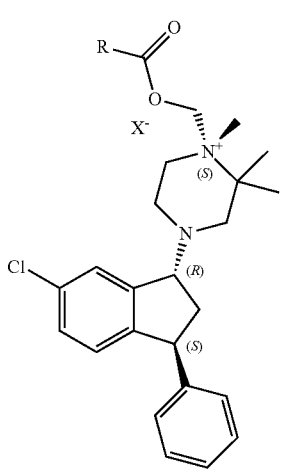

1b

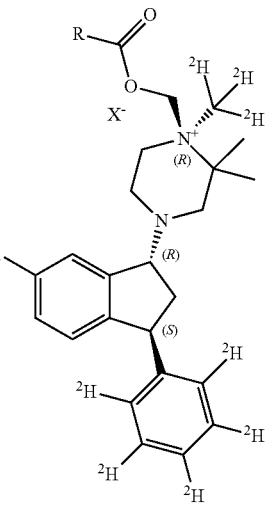

2a

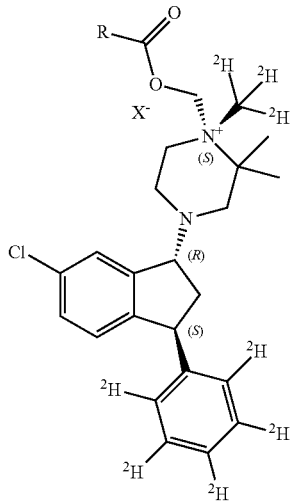

2b 1a and 2a are R-configured at the chiral nitrogen atom, while 1b and 2b are S-configured at the chiral nitrogen atom.

R is linear or branched $C_1$-$C_{11}$ alkyl, such as methyl; or $C_3$-$C_{10}$ cycloalkyl, such as cyclohexylmethyl or cyclohexylethyl.

—$CH_2OC(O)R$ attached to 4-((1R,3S)-6-chloro-3-phenyl-2,3-dihydro-1H-inden-1-yl)-1,2,2-trimethylpiperazine or 4-((1R,3S)-6-chloro-3-(phenyl-$d_5$)-2,3-dihydro-1H-inden-1-yl)-2,2-dimethyl-1-(methyl-$d_3$)piperazine is referred to as the prodrug group.

$X^-$ is selected from the group consisting of halide anion, such as chloride, bromide or iodide, $C_1$-$C_{10}$ sulfonate, optionally fluorinated, such as mesylate, tosylate, trifluoromethanesulfonate or nonafluorobutanesulfonate, and linear or branched $C_1$-$C_{11}$ carboxylate, optionally fluorinated, such as trifluoroacetate.

Compounds 1a and 1b have the natural hydrogen isotope distribution, while 2a and 2b are enriched in deuterium ($^2H$) at the indicated positions.

Prodrug

A prodrug in general is a compound which may not have any pharmacological activity itself, but which upon administration to a patient is metabolised to provide a pharmacologically active compound. More specifically, a prodrug of the present invention is a compound which upon administration to a patient is metabolised to provide 4-((1R,3S)-6-chloro-3-phenyl-2,3-dihydro-1H-inden-1-yl)-1,2,2-trimethylpiperazine (prodrugs 1a and 1b) or 4-((1R,3S)-6-chloro-3-(phenyl-d$_5$)-2,3-dihydro-1H-inden-1-yl)-2,2-dimethyl-1-(methyl-d$_3$)piperazine (prodrugs 2a and 2b).

Salts

Some of the prodrugs of the present invention may be provided as pharmaceutically acceptable acid addition salts. The term pharmaceutically acceptable salts includes salts formed with inorganic and/or organic acids such as hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid. Di- and tri-acids may form 1:1, 1:2 or 1:3 (tri-acids) salts, i.e. a salt formed between two or three molecules of the compound of the present invention and one molecule of the acid. Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Therapeutically Effective Amount

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. A prodrug of the present invention is typically administered to achieve therapeutic effect comparable to the administration of 1-60 mg 4-((1R,3S)-6-chloro-3-phenyl-2,3-dihydro-1H-inden-1-yl)-1,2,2-trimethylpiperazine or 4-((1R,3S)-6-chloro-3-(phenyl-d$_5$)-2,3-dihydro-1H-inden-1-yl)-2,2-dimethyl-1-(methyl-d$_3$)piperazine, such as 1-30 mg 4-((1R,3S)-6-chloro-3-phenyl-2,3-dihydro-1H-inden-1-yl)-1,2,2-trimethylpiperazine or 4-((1R,3S)-6-chloro-3-(phenyl-d$_5$)-2,3-dihydro-1H-inden-1-yl)-2,2-dimethyl-1-(methyl-d$_3$) piperazine, such as 5 mg, 10 mg, 15 mg or 20 mg calculated as the free base. This means e.g. that "20 mg 4-((1R,3S)-6-chloro-3-phenyl-2,3-dihydro-1H-inden-1-yl)-1,2,2-trimethylpiperazine or 4-((1R,3S)-6-chloro-3-(phenyl-d$_5$)-2,3-dihydro-1H-inden-1-yl)-2,2-dimethyl-1-(methyl-d$_3$) piperazine" means 20 mg 4-((1R,3S)-6-chloro-3-phenyl-2,3-dihydro-1H-inden-1-yl)-1,2,2-trimethylpiperazine or 4-((1R,3S)-6-chloro-3-(phenyl-d$_5$)-2,3-dihydro-1H-inden-1-yl)-2,2-dimethyl-1-(methyl-d$_3$)piperazine free base where the actual amount administered has to be adjusted for the weight of the prodrug group and further adjusted for the weight of the counter ion.

In the present context, "treatment" or "treating" is intended to indicate the management and care of a patient for the purpose of alleviating, arresting, partly arresting or delaying progress of the clinical manifestation of the disease, or curing the disease. The patient to be treated is preferably a mammal, in particular a human being.

Diseases

In the present context, "CNS disease" is intended to indicate a disease in the central nervous system. As disclosed in e.g. WO 2005/016900 and WO 2012/176066 the pharmacological profile of 4-((1R,3S)-6-chloro-3-phenyl-2,3-dihydro-1H-inden-1-yl)-1,2,2-trimethylpiperazine and 4-((1R,3S)-6-chloro-3-(phenyl-d$_5$)-2,3-dihydro-1H-inden-1-yl)-2,2-dimethyl-1-(methyl-d$_3$)piperazine (i.e. the parent form of 1a, 1b, 2a and 2b) is expected to also make the compound useful in the treatment of CNS diseases, including but not limited to psychosis, in particular schizophrenia or other diseases involving psychotic symptoms, such as, e.g., Schizophrenia, Treatment Resistant Schizophrenia (TRS) Schizophreniform Disorder, Schizoaffective Disorder, Delusional Disorder, Brief Psychotic Disorder, Shared Psychotic Disorder as well other psychotic disorders or diseases that present with psychotic symptoms, e.g. bipolar disorder, such as mania in bipolar disorder. Compounds and/or compositions of the invention can further be used in treatment of disorders such as those described in, for example, U.S. Pat. Nos. 5,807,855; 7,648,991; 7,767,683; 7,772,240; 8,076,342; U.S. Patent Publication Nos. 2008/0269248; 2010/0069676; 2011/0178094; 2011/0207744; WO 2005/016900; EP 0 638 073; and *J. Med. Chem.* 1995, 38, 4380-4392; each herein incorporated by reference in its entirety. The invention also relates to the medical use of compounds of the present invention as combination therapy in conjunction with other therapeutic agents such as those described in, for example, U.S. Pat. Nos. 5,807,855; 7,648,991; 7,767,683; 7,772,240; 8,076,342; U.S. Patent Publication Nos. 2008/0269248; 2010/0069676; 2011/0178094; 2011/0207744; WO 2005/016900; EP 0 638 073; and *J. Med. Chem.* 1995, 38, 4380-4392; each herein incorporated by reference in its entirety.

In the present context Treatment Resistant Schizophrenia is intended to indicate a lack of satisfactory clinical improvement despite two treatments with antipsychotics of adequate dose and duration.

Pharmaceutical Composition

The pharmaceutical compositions may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

In the present context, the term "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a 4-((1R,3S)-6-chloro-3-phenyl-2,3-dihydro-1H-inden-1-yl)-1,2,2-trimethylpiperazine prodrug (1a and 1b) or 4-((1R,3S)-6-chloro-3-(phenyl-d$_5$)-2,3-dihydro-1H-inden-1-yl)-2,2-dimethyl-1-(methyl-d$_3$) piperazine prodrug (2a and 2b) or a pharmaceutically acceptable salt thereof. The pharmaceutical compositions according to the invention may be formulated with pharmaceutically acceptable excipients in accordance with conventional techniques such as those disclosed in Remington, The Science and Practice of Pharmacy, 22$^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid. Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose.

If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, polysorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Embodiments of the Invention

The invention is described further in the following embodiments:

1. A prodrug of 4-((1R,3S)-6-chloro-3-phenyl-2,3-dihydro-1H-inden-1-yl)-1,2,2-trimethylpiperazine (in the form of 1a and 1b) or 4-((1R,3S)-6-chloro-3-(phenyl-d$_5$)-2,3-dihydro-1H-inden-1-yl)-2,2-dimethyl-1-(methyl-d$_3$)piperazine (in the form of 1a and 1b)

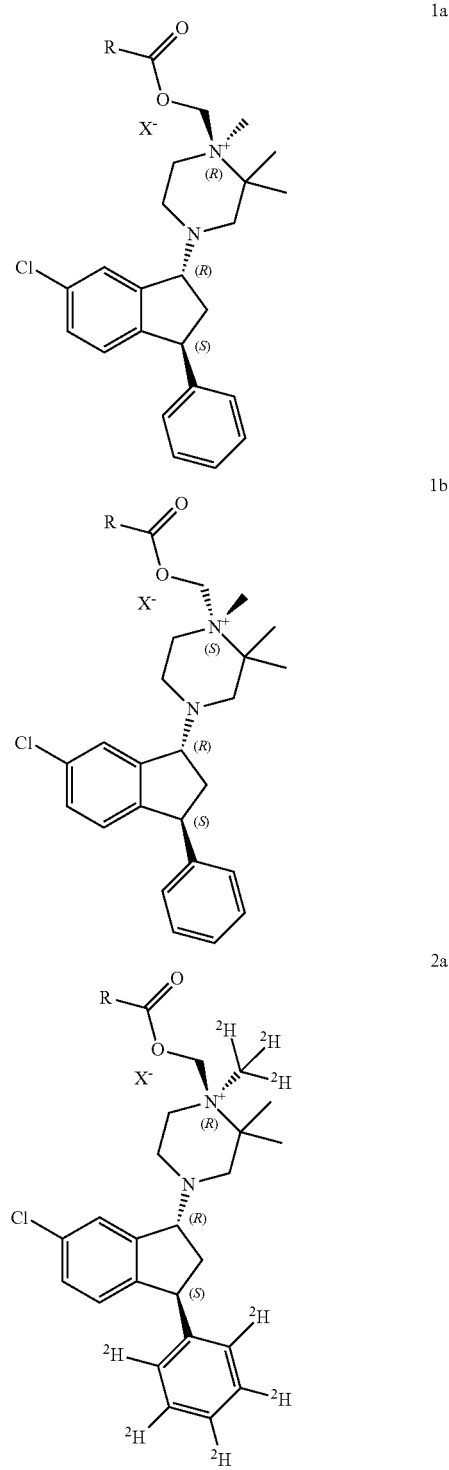

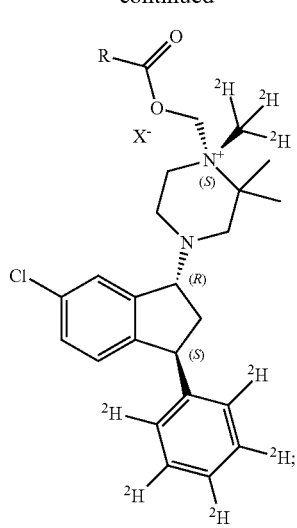

wherein X⁻ is a counter ion selected from the group consisting of a halide anion, such as chloride, bromide or iodide, $C_1$-$C_{10}$ sulfonate, optionally fluorinated, such as mesylate, tosylate, trifluoromethanesulfonate or nonafluorobutanesulfonate, and linear or branched $C_1$-$C_{11}$ carboxylate, optionally fluorinated, such as trifluoroacetate; or a pharmaceutically acceptable salt thereof.

2. The prodrug according to embodiment 1, wherein R is selected from the group consisting of linear or branched $C_1$-$C_{11}$ alkyl and $C_3$-$C_{10}$ cycloalkyl, or a pharmaceutically acceptable salt thereof.

3. The prodrug according to any of embodiments 1 and 2, wherein R is selected from the group consisting of methyl, tertbutyl, n-undecane and cyclohexylmethyl, or a pharmaceutically acceptable salt thereof.

4. The prodrug according to any of embodiments 1 to 3, wherein the pharmaceutically acceptable salt is formed from hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid, saccharin and sulfonic acids, such as methanesulfonic acid, ethanesulfonic acid, toluenesulfonic acid and benzenesulfonic acid.

5. The prodrug according to any of embodiments 1 to 4 selected from the group consisting of (R)-1-(acetoxymethyl)-4-((1R,3S)-6-chloro-3-phenyl-2,3-dihydro-1H-inden-1-yl)-1,2,2-trimethylpiperazin-1-ium, (S)-1-(acetoxymethyl)-4-((1R,3S)-6-chloro-3-phenyl-2,3-dihydro-1H-inden-1-yl)-1,2,2-trimethylpiperazin-1-ium, (R)-1-(acetoxymethyl)-4-((1R,3S)-6-chloro-3-(phenyl-d₅)-2,3-dihydro-1H-inden-1-yl)-2,2-dimethyl-1-(methyl-d₃)piperazin-1-ium, (S)-1-(acetoxymethyl)-4-((1R,3S)-6-chloro-3-(phenyl-d₅)-2,3-dihydro-1H-inden-1-yl)-2,2-dimethyl-1-(methyl-d₃)piperazin-1-ium, (R)-4-((1R,3S)-6-chloro-3-phenyl-2,3-dihydro-1H-inden-1-yl)-2,2-dimethyl-1-((pivaloyloxy)methyl)piperazin-1-ium, (S)-4-((1R,3S)-6-chloro-3-phenyl-2,3-dihydro-1H-inden-1-yl)-2,2-dimethyl-1-methyl-1-((pivaloyloxy)methyl)piperazin-1-ium, (R)-4-((1R,3S)-6-chloro-3-(phenyl-d₅)-2,3-dihydro-1H-inden-1-yl)-2,2-dimethyl-1-(methyl-d₃)-1-((pivaloyloxy)methyl)piperazin-1-ium, (S)-4-((1R,3S)-6-chloro-3-(phenyl-d₅)-2,3-dihydro-1H-inden-1-yl)-2,2-dimethyl-1-(methyl-d₃)-1-((pivaloyloxy)methyl)piperazin-1-ium, (R)-4-((1R,3S)-6-chloro-3-phenyl-2,3-dihydro-1H-inden-1-yl)-1-((dodecanoyloxy)methyl)-1,2,2-trimethylpiperazin-1-ium, (S)-4-((1R,3S)-6-chloro-3-phenyl-2,3-dihydro-1H-inden-1-yl)-1-((dodecanoyloxy)methyl)-1,2,2-trimethylpiperazin-1-ium, (R)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃)piperazin-1-ium, (S)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃)piperazin-1-ium, (R)-4-((1R,3S)-6-chloro-3-phenyl-2,3-dihydro-1H-inden-1-yl)-1-((2-cyclohexylacetoxy)methyl)-1,2,2-trimethylpiperazin-1-ium, (S)-4-((1R,3S)-6-chloro-3-phenyl-2,3-dihydro-1H-inden-1-yl)-1-((2-cyclohexylacetoxy)methyl)-1,2,2-trimethylpiperazin-1-ium, (R)-4-((1R,3S)-6-chloro-3-(phenyl-d₅)-2,3-dihydro-1H-inden-1-yl)-1-((2-cyclohexylacetoxy)methyl)-2,2-dimethyl-1-(methyl-d₃)piperazin-1-ium, (S)-4-((1R,3S)-6-chloro-3-(phenyl-d₅)-2,3-dihydro-1H-inden-1-yl)-1-((2-cyclohexylacetoxy)methyl)-2,2-dimethyl-1-(methyl-d₃)piperazin-1-ium, each of which is combined with a counter ion selected from the group consisting of halide anion, such as chloride, bromide or iodide, $C_1$-$C_{10}$ sulfonate, optionally fluorinated, such as mesylate, tosylate, trifluoromethanesulfonate or nonafluorobutanesulfonate, and linear or branched $C_1$-$C_{11}$ carboxylate, optionally fluorinated, such as trifluoroacetate; or a pharmaceutically acceptable salt thereof.

6. A pharmaceutical composition comprising any of the prodrugs of embodiments 1 to 5, or a pharmaceutically acceptable salt thereof, and one or more pharmaceutically acceptable excipients.

7. The compound according to any of embodiments 1 to 5, or a pharmaceutically acceptable salt thereof, or the pharmaceutical composition according to embodiment 6 for use in therapy.

8. Use of a compound according to any of embodiments 1 to 5 or a salt thereof, or a pharmaceutical composition according to embodiment 6 for the manufacture of a medicament for the treatment of a Central Nervous System (CNS) disease.

9. A compound according to any of embodiments 1 to 5 or a pharmaceutical composition according to embodiment 6 for use in a method for the treatment of a CNS disease.

10. A method for the treatment of a CNS disease, the method comprising the administration of a therapeutically effective amount of a compound according to any of embodiments 1 to 5 or a pharmaceutical composition according to embodiment 6 to a patient in need thereof.

EXAMPLES

Compounds of the Invention

The compounds of the invention can be prepared from either 4-((1R,3S)-6-chloro-3-phenyl-2,3-dihydro-1H-inden-1-yl)-1,2,2-trimethylpiperazine (1) or 4-((1R,3S)-6-chloro-3-(phenyl-d₅)-2,3-dihydro-1H-inden-1-yl)-2,2-dimethyl-1-(methyl-d₃)piperazine (2) both of which are described in the prior art as discussed above:

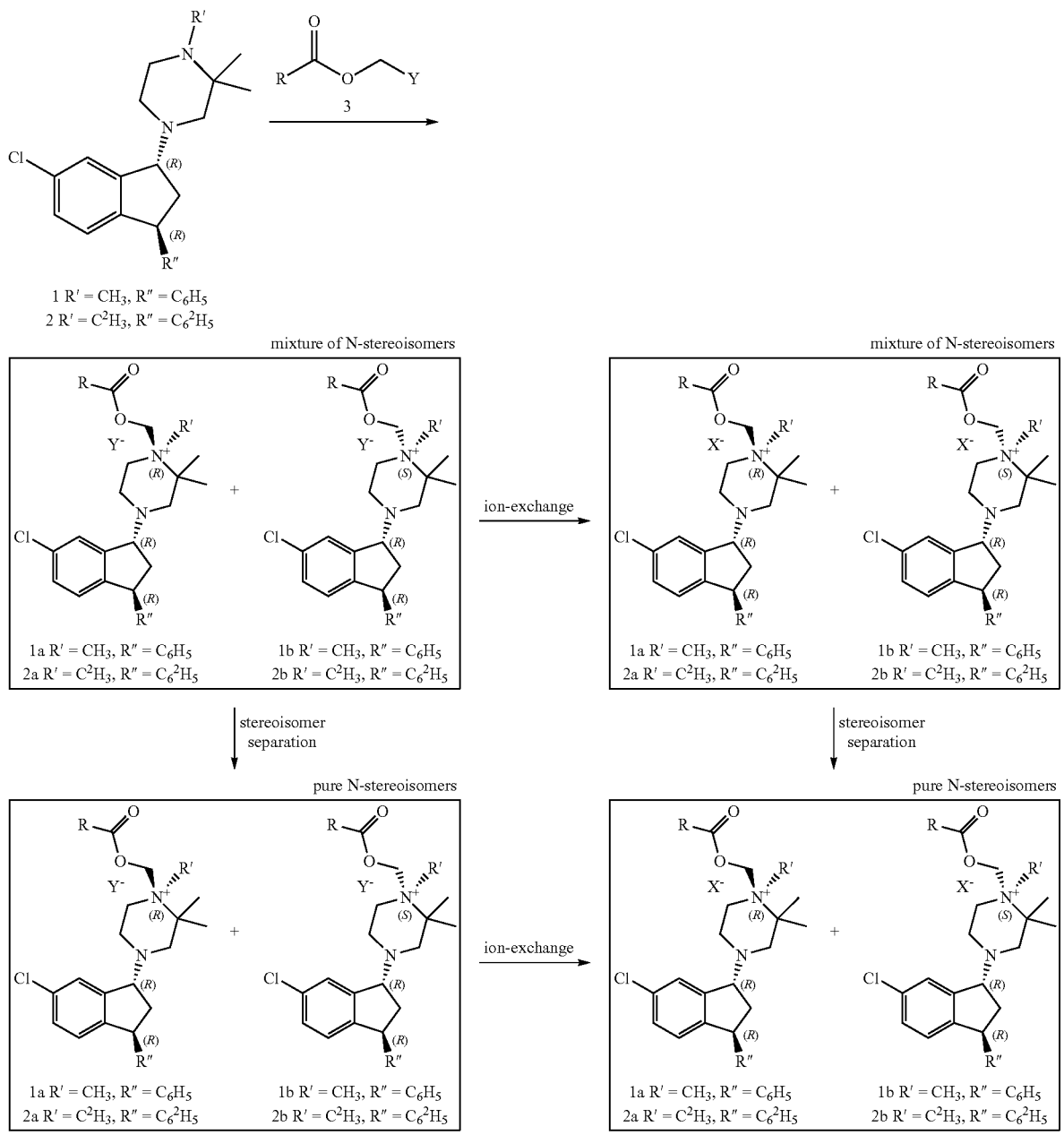

These compounds can be alkylated at the non-benzylic piperazine nitrogen atom by treatment with alkylating agents 3 either directly or via in-situ Finkelstein displacement of Y with a more reactive halogen such as conversion from Y=Cl to Y=I by addition of sodium iodide or from Y=Cl to Y=Br by addition of tetra-n-butyl ammonium bromide or sodium bromide. The reaction will afford a mixture of N-diastereoisomers 1a/1b or 2a/2b, depending on whether 1 or 2 is employed as substrate. These N-diastereoisomers can be separated either by recrystallization and/or by chiral chromatography using either high-performance liquid chromatography (HPLC), super-critical fluid chromatography (SFC), or simulated moving bed chromatography (SMB). The anion $Y^-$ can be exchanged with $X^-$ using for example ion exchange resin. $Y^-$ can be selected from the same list as $X^-$ as defined above. The order of the last two operations can be reversed, and both steps can be performed several times. The alkylating agents 3 are either commercially available such as 3b from CombiBlocks (catalog number QC-7757) or can be prepared in a similar manner as described in the specification for 3a or as described in the literature (for sulfonates, see e.g. WO 2012/137225).

Methods Employed in the Preparation of the Prodrugs of the Invention.

The following methods were employed for high-performance liquid chromatography (HPLC), liquid chromatography/mass spectrometry (LC/MS), supercritical fluid chromatography (SFC), and ion exchange.

Method 1:

HPLC performed on a Agela-HP-q-p600 instrument fitted with a Agela Innoval ods 250×80 mm column (10 microm particle size; column temperature 20° C.). Eluent: 0.05% aq. HCl/acetronitrile 4:1 to 1:1 over 20 min with a flow rate of 150 mL/min.

Method 2:

LC/MS performed on a Agilent 1200 & 1956A Instrument fitted with a Phenomenex Luna C18(2) 50×2 mm column (5 microm particle size; column temperature 40° C.). Eluent: 0.037% trifluoroacetic acid in water/0.018% trifluoroacetic acid in acetonitrile 1:0 for 0.8 min; 1:0 to 2:3 over 6.2 min; 2:3 for 3 min; 2:3 to 1:0 over 0.1 min with a flow rate of 0.6 mL/min.

Method 3:

HPLC performed on a Agela-HP-q-p600 instrument fitted with a Phenomenex Luna C18 250×50 mm column (10 microm particle size; column temperature 20° C.). Eluent: 0.05% aq. HCl/acetronitrile 4:1 to 1:1 over 20 min with a flow rate of 80 mL/min.

Method 4:

SFC performed with stacked injections on a Thar SFC80 preparative instrument fitted with a Chiralpak AD-H 250×30 mm column (particle size 5 microm) operated at 40° C. Eluent: $CO_2$/0.1% trifluoroacetic acid in methanol 7:3 for 5 min with a flow rate of 70 g/min. System back pressure 100 bar.

Method 5:

SFC performed on a Thar Analytical SFC instrument fitted with a Chiralpak AD-3 100×4.6 mm column (particle size 3 microm; column temperature 40° C.). Eluent: $CO_2$/0.05% isopropyl amine in methanol 95:5 to 3:2 over 5 min with a flow rate of 4.0 mL/min. System back pressure 100 bar.

Method 6:

SFC Performed as method 4 with a run time of 7 min.

Method 7:

LC/MS performed on a Agilent 1200 & MS 1956A Instrument fitted with a Phenomenex Luna C18(2) 50×2 mm column (5 microm particle size; column temperature 40° C.). Eluent: 0.037% trifluoroacetic acid in water/0.018% trifluoroacetic acid in acetonitrile 9:1 for 0.4 min; 9:1 to 0:1 over 3.0 min; 0:1 for 0.45 min; 0:1 to 9:1 over 0.01 min; 9:1 for 0.64 min with a flow rate of 0.8 mL/min.

Method 8:

HPLC performed as method 3 but with 3:2 to 3:7 eluent gradient over 20 min.

Method 9:

SFC performed with stacked injections on a Thar SFC80 preparative instrument fitted with a Chiralpak AD-H 250×30 mm column (particle size 5 microm; column temperature 40° C.). Eluent: $CO_2$/0.1% trifluoroacetic acid in methanol 4:1 for 6 min with a flow rate of 70 g/min. System back pressure 100 bar.

Method 10:

SFC performed on a Waters Acquity UPC2 instrument fitted with a Chiralpak AD-3 150×4.6 mm column (particle size 3 microm; column temperature 35° C.). Eluent: $CO_2$/0.05% isopropyl amine in methanol 3:2 over 6 or 10 min with a flow rate of 2.5 mL/min. System back pressure 1500 psi.

Method 11:

Ion exchange performed using anion exchange resins in chloride form (717; Domestic 10024160) ion exchange resin. The sample was dissolved in a 1:1 mixture of acetonitrile and water and the solution was allowed to pass slowly through a column with the resin (using ca six times as much resin and sample). Acetonitrile/water (1:1) was added until all sample had been eluted. The combined product fractions were concentrated in vacuo and freeze-dried to afford the chloride salts of the compound(s).

Method 12:

LC/MS performed on a Agilent 1200 & MS 1956A Instrument fitted with a Phenomenex Luna C18(2) 50×2 mm column (5 microm particle size; column temperature 40° C.). Eluent: 0.037% trifluoroacetic acid in water/0.018% trifluoroacetic acid in acetonitrile 99:1 to 1:9 over 3.4 min; 1:9-0:1 over 0.45 min; 0:1 to 99:1 over 0.01 min; 991:1 for 0.64 min with a flow rate of 0.8 mL/min.

Method 13:

LC/MS performed on a Agilent 1200 & MS 1956A Instrument fitted with a Phenomenex Luna C18(2) 50×2 mm column (5 microm particle size; column temperature 40° C.). Eluent: 0.037% trifluoroacetic acid in water/0.018% trifluoroacetic acid in acetonitrile 3:2 to 0:1 over 3.4 min; 0:1 for 0.45 min; 0:1 to 3:2 over 0.01 min; 3:2 for 0.64 min with a flow rate of 0.8 mL/min.

Method 14:

LC/MS performed on a Agilent 1200 & MS 6120 Instrument fitted with a Phenomenex Luna C18(2) 50×2 mm column (5 microm particle size; column temperature 40° C.). Eluent: 0.037% trifluoroacetic acid in water/0.018% trifluoroacetic acid in acetonitrile 3:1 to 0:1 over 3.4 min; 0:1 for 0.45 min; 0:1 to 3:1 over 0.01 min; 3:1 for 0.64 min with a flow rate of 0.8 mL/min.

Method 15:

LC/MS performed on a Agilent 1200 & MS 6120B Instrument fitted with a Phenomenex Luna C18(2) 50×2 mm column (5 microm particle size; column temperature 40° C.). Eluent: 0.037% trifluoroacetic acid in water/0.018% trifluoroacetic acid in acetonitrile 9:1 to 1:4 over 4.0 min; 1:4 for 2.0 min; 1:4 to 9:1 over 0.01 min; 9:1 for 2.0 min with a flow rate of 0.8 mL/min.

Method 16:

SFC performed as method 9 with a run time of 8 min.

Method 17:

LC/MS performed on a Agilent 1200 & MS 1956A Instrument fitted with a Phenomenex Luna C18(2) 50×2 mm column (5 microm particle size; column temperature 40° C.). Eluent: 0.037% trifluoroacetic acid in water/0.018% trifluoroacetic acid in acetonitrile 1:0 for 0.8 min; 1:0 to 2:3 over 6.2 min; 2:3 for 3 min; 2:3 to 1:0 over 0.1 min with a flow rate of 0.8 mL/min.

Method 18:

Reverse-phase column chromatography performed on a Biotage One instrument fitted with a Agela 40×10 cm (20-40 nM) C18 column at 25° C. Eluent: water and 0.4% concentrated hydrochloric acid 7:3 to 3:7 over 30 min; 3:7 for 25 min; 0:1 for 10 min with a flow rate of 120 mL/min.

Example 1: Preparation of Iodomethyl Acetate (Alkylating Agent 3a)

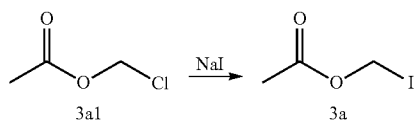

To a mixture of NaI (29.0 g) and acetonitrile (140 mL) was added chloromethyl acetate (3a1; 20.0 g) dropwise at 20° C. in the dark. The reaction was stirred at ambient temperature for 24 hours. The resulting mixture was partitioned between methyl tert-butyl ether (MTBE; 160 mL) and water (200 mL), and the aqueous layer was extracted with MTBE (150 mL). The combined organic layers were washed successively with saturated aqueous sodium bicarbonate (200 mL), 10 percent aqueous sodium sulfite solution (200 mL), and saturated aqueous sodium chloride (100 mL) before it was dried over sodium sulphate, filtered, and concentrated to afford iodomethyl acetate (3a; 15.5 g) sufficiently pure for the next step.

Example 2: Preparation of Iodomethyl n-Dodecanoate (Alkylating Agent 3c)

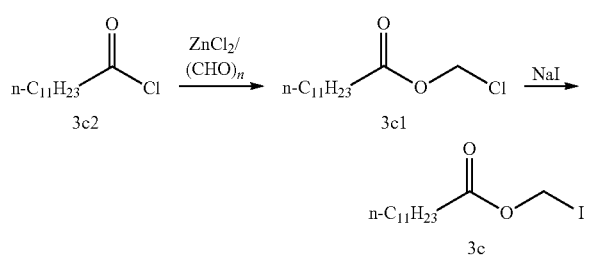

n-Dodecanoyl chloride (3c2; 80.0 g) was added slowly to a mixture of paraformaldehyde (22.0 g) and zinc chloride (24.9 g) in acetonitrile (550 mL) at −10° C. under an argon atmosphere. The reaction mixture was stirred at this temperature for 1 hour and at ambient temperature for 18 hours. The crude reaction mixture was directly purified by column flash chromatography on silica gel (gradient eluent: petroleum ether/ethyl acetate 50/1 to 2/1) to afford chloromethyl n-dodecanoate (3c1; 45.4 g) sufficiently pure for the next step. To a mixture of sodium iodide (32.5 g) in acetonitrile (300 mL) was added compound 3c1 (45.0 g) dropwise at ambient temperature in the dark. The reaction was stirred at ambient temperature for 24 hours. The crude mixture was partitioned between MTBE (300 mL) and water (300 mL), and the aqueous layer was extracted with MTBE (100 mL). The combined organic layers were washed successively with saturated aqueous sodium bicarbonate (200 mL), 10 percent aqueous sodium sulfite solution (150 mL), and saturated aqueous sodium chloride (150 mL) before it was dried over sodium sulphate, filtered, and concentrated to afford iodomethyl n-dodecanoate (3c; 51.0 g) sufficiently pure for the next step.

Example 3: Preparation of Iodomethyl 2-cyclo-hexylacetate (Alkylating Agent 3d)

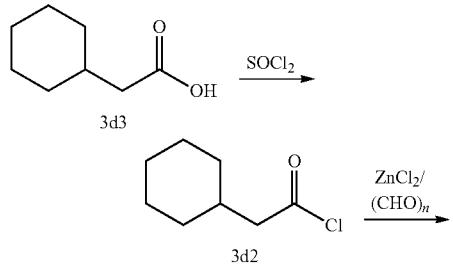

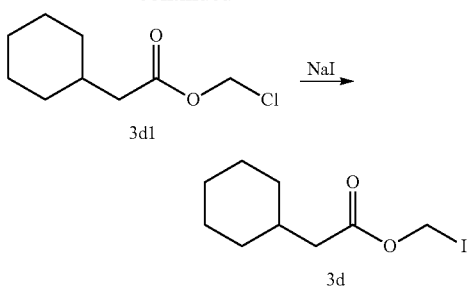

Thionyl chloride (69 mL) was added to a solution of 2-cyclo-hexylacetic acid (3d3; 44.8 g) in toluene (180 mL) under an argon atmosphere, and the mixture was stirred at 110° C. for 12 hours. The volatiles were removed in vacuo to afford 2-cyclo-hexylacetyl chloride (3d2; 42.3 g) sufficiently pure for the next step. 2-Cyclo-hexylacetyl chloride (3d2; 48.6 g—combined material from the previous step and another batch) was added to a solution of zinc chloride (20.6 g) and paraformaldehyde (18.2 g) in acetonitrile (336 mL) at −10° C. under an argon atmosphere. The reaction mixture was stirred at −10° C. for one hour and then at ambient temperature for 18 hours. The volatiles were removed in vacuo. The residue was purified by column flash chromatography on silica gel (gradient eluent: petroleum ether/ethyl acetate 1/0 to 0/1) to afford chloromethyl 2-cyclo-hexylacetate (3d1; 24.0 g) sufficiently pure for the next step. To a solution of sodium iodide (18.1 g) in acetonitrile (126 mL) was added 2-cyclo-hexylacetate (3d1; 21.9 g) dropwise at ambient temperature in the dark. The reaction was stirred at ambient temperature for 24 hours. The crude mixture was partitioned between MTBE (200 mL) and water (200 mL), and the aqueous layer was extracted with MTBE (150 mL). The combined organic layers were washed successively with saturated aqueous sodium bicarbonate (200 mL), 10 percent aqueous sodium sulfite solution (200 mL), and saturated aqueous sodium chloride (100 mL) before it was dried over sodium sulphate, filtered, and concentrated to afford iodomethyl 2-cyclo-hexylacetate (3d; 27.0 g) sufficiently pure for the next step.

Example 4: Preparation of Acetoxymethyl 1a and 1b

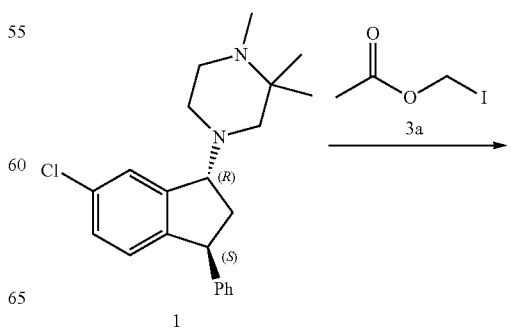

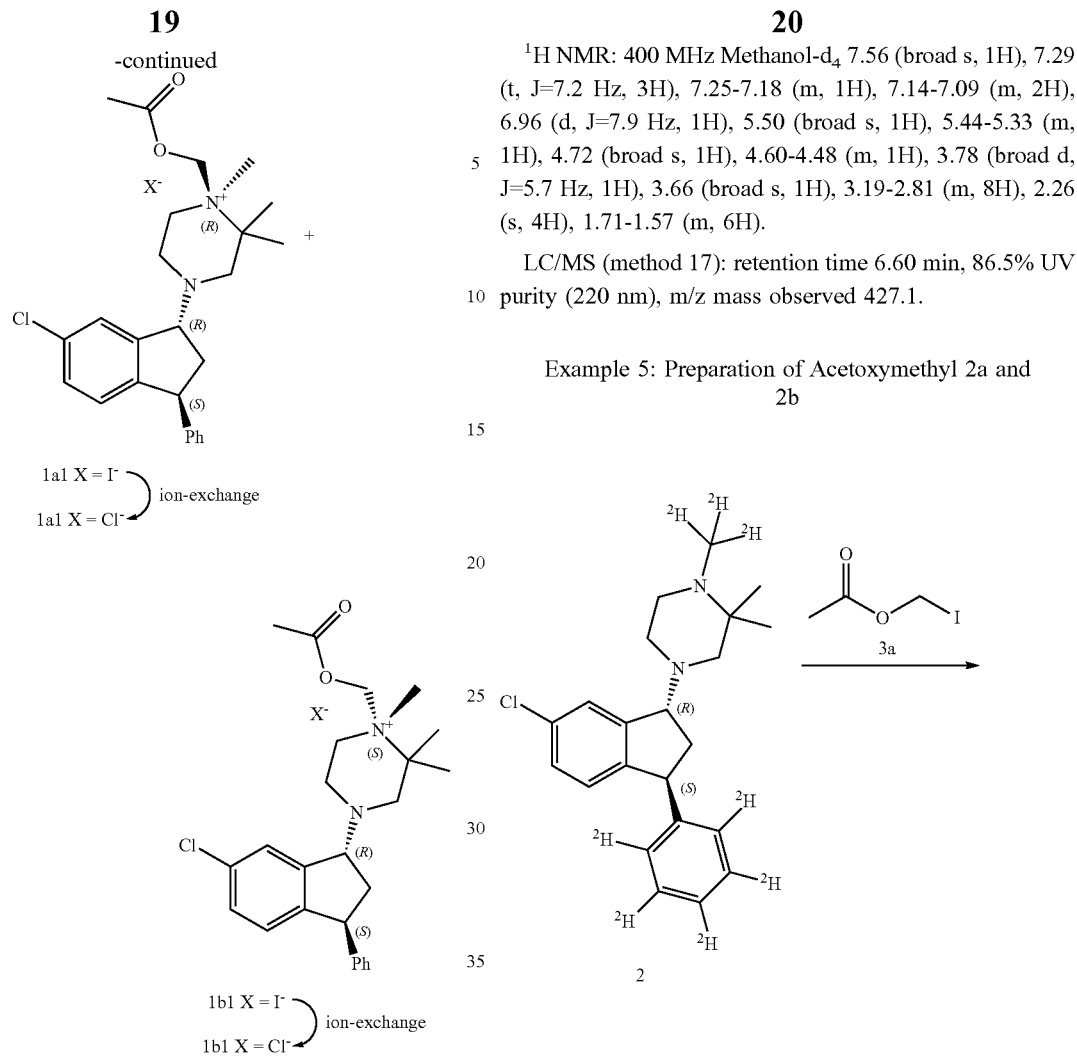

1a1 X = I⁻ ⎫
1a1 X = Cl⁻ ⎬ ion-exchange

1b1 X = I⁻ ⎫
1b1 X = Cl⁻ ⎬ ion-exchange

A solution of 4-((1R,3S)-6-chloro-3-phenyl-2,3-dihydro-1H-inden-1-yl)-1,2,2-trimethylpiperazine (1; 6.0 g) in acetonitrile (42 mL) was heated to 80° C. before iodomethyl acetate (3a; 6.76 g) was added. The mixture was stirred at 80° C. for 1 hour before the volatiles were removed in vacuo. The residual solid was suspended in MTBE (25 mL) and then filtered off. The filter cake was washed with MTBE (15 mL) and dried to afford ca. 8 g of a mixture of (R)-1-(acetoxymethyl)-4-((1R,3S)-6-chloro-3-phenyl-2,3-dihydro-1H-inden-1-yl)-1,2,2-trimethylpiperazin-1-ium iodide (1a1; X=I⁻) and (S)-1-(acetoxymethyl)-4-((1R,3S)-6-chloro-3-phenyl-2,3-dihydro-1H-inden-1-yl)-1,2,2-trimethylpiperazin-1-ium iodide (1b1; X=I⁻). This material was converted from the iodide salt to the corresponding chloride salts by ion exchange (method 11) to afford the crude chloride salts of 1a1; X=Cl⁻ and 1b1; X=Cl⁻. This material was purified by preparative HPLC (method 1) to give a mixture of (R)-1-(acetoxymethyl)-4-((1R,3S)-6-chloro-3-phenyl-2,3-dihydro-1H-inden-1-yl)-1,2,2-trimethylpiperazin-1-ium chloride and (S)-1-(acetoxymethyl)-4-((1R,3S)-6-chloro-3-phenyl-2,3-dihydro-1H-inden-1-yl)-1,2,2-trimethylpiperazin-1-ium chloride (1a1; X=Cl⁻ and 1b1; X=Cl⁻; 3 g).

¹H NMR: 400 MHz Methanol-$d_4$ 7.56 (broad s, 1H), 7.29 (t, J=7.2 Hz, 3H), 7.25-7.18 (m, 1H), 7.14-7.09 (m, 2H), 6.96 (d, J=7.9 Hz, 1H), 5.50 (broad s, 1H), 5.44-5.33 (m, 1H), 4.72 (broad s, 1H), 4.60-4.48 (m, 1H), 3.78 (broad d, J=5.7 Hz, 1H), 3.66 (broad s, 1H), 3.19-2.81 (m, 8H), 2.26 (s, 4H), 1.71-1.57 (m, 6H).

LC/MS (method 17): retention time 6.60 min, 86.5% UV purity (220 nm), m/z mass observed 427.1.

Example 5: Preparation of Acetoxymethyl 2a and 2b

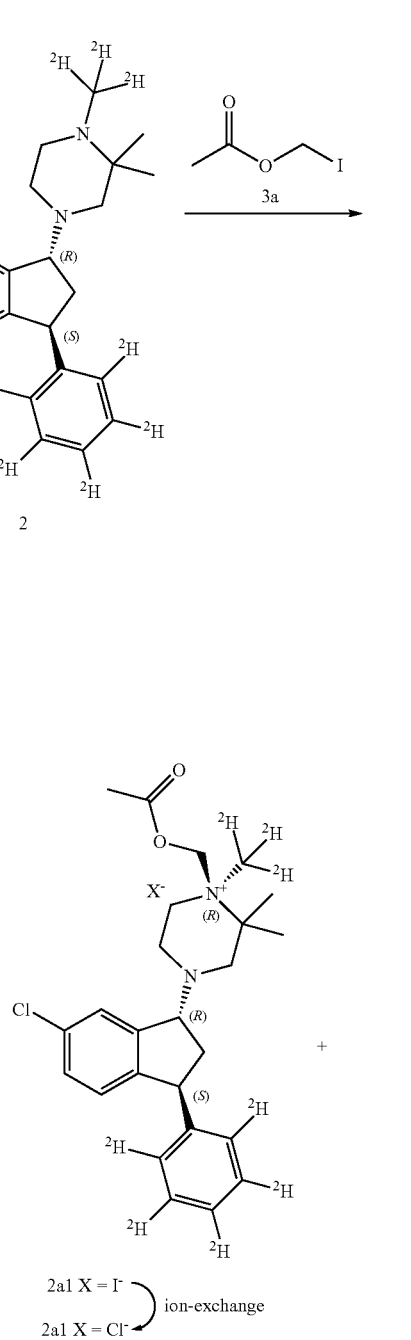

2a1 X = I⁻ ⎫
2a1 X = Cl⁻ ⎬ ion-exchange

-continued

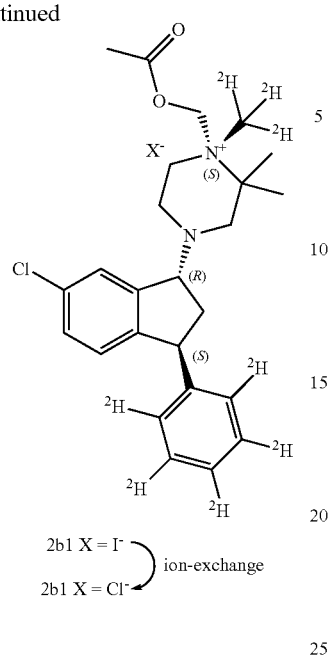

2b1 X = I⁻  
2b1 X = Cl⁻  } ion-exchange

Mixtures of (R)-1-(acetoxymethyl)-4-((1R,3S)-6-chloro-3-(phenyl-d₅)-2,3-dihydro-1H-inden-1-yl)-2,2-dimethyl-1-(methyl-d₃)piperazin-1-ium iodide and (S)-1-(acetoxymethyl)-4-((1R,3S)-6-chloro-3-(phenyl-d₅)-2,3-dihydro-1H-inden-1-yl)-2,2-dimethyl-1-(methyl-d₃)piperazin-1-ium iodide (2a1; X=I⁻ and 2b1; X=I⁻) and (R)-1-(acetoxymethyl)-4-((1R,3S)-6-chloro-3-(phenyl-d₅)-2,3-dihydro-1H-inden-1-yl)-2,2-dimethyl-1-(methyl-d₃)piperazin-1-ium chloride and (S)-1-(acetoxymethyl)-4-((1R,3S)-6-chloro-3-(phenyl-d₅)-2,3-dihydro-1H-inden-1-yl)-2,2-dimethyl-1-(methyl-d₃)piperazin-1-ium chloride (2a1; X=Cl⁻ and 2b1; X=Cl⁻) were prepared in a similar manner as 1a1 and 1b1. The synthesis started from 4-((1R,3S)-6-chloro-3-(phenyl-d₅)-2,3-dihydro-1H-inden-1-yl)-2,2-dimethyl-1-(methyl-d₃)piperazine (2; 6.50 g) and iodomethyl acetate (3a; 7.16 g) in acetonitrile (45.0 mL) to afford ca. 8 g of crude iodide and 2.00 g of HPLC-purified (method 1) mixture of (R)-1-(acetoxymethyl)-4-((1R,3S)-6-chloro-3-(phenyl-d₅)-2,3-dihydro-1H-inden-1-yl)-2,2-dimethyl-1-(methyl-d₃)piperazin-1-ium chloride and (S)-1-(acetoxymethyl)-4-((1R,3S)-6-chloro-3-(phenyl-d₅)-6-chloro-3-(phenyl-d₅)-2,3-dihydro-1H-inden-1-yl)-2,2-dimethyl-1-(methyl-d₃)piperazin-1-ium chloride (2a1; X=Cl⁻ and 2b1; X=Cl⁻).

¹H NMR: 400 MHz Methanol-d₄ 7.61-7.54 (m, 1H), 7.34-7.28 (m, 1H), 6.96 (d, J=8.3 Hz, 1H), 5.51 (broad d, J=12.7 Hz, 1H), 5.47-5.35 (m, 1H), 4.74 (broad s, 1H), 4.56 (broad s, 1H), 3.77 (broad s, 1H), 3.68 (broad s, 1H), 3.27-2.78 (m, 5H), 2.26 (d, J=0.9 Hz, 4H), 1.73-1.58 (m, 6H).

LC/MS (method 17): retention time 6.56 min, 93.5% UV purity (220 nm), m/z mass observed 435.2.

Example 6: Preparation of Pivaloyloxymethyl 1a and 1b

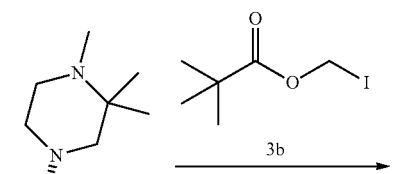

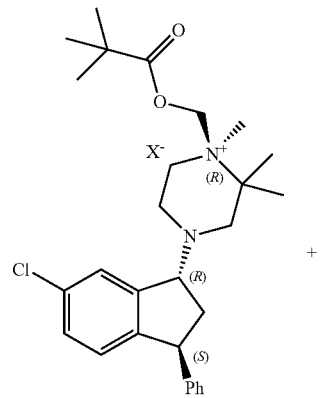

1a2 X = I⁻  } ion-exchange
1a2 X = Cl⁻ (mixture)  } chiral SFC / ion-exchange
1a2 X = Cl⁻ (pure stereoisomer)

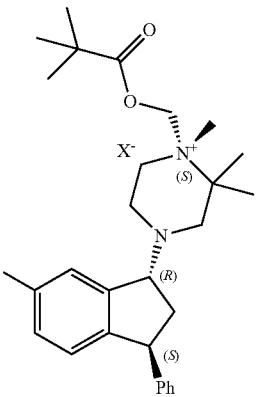

1b2 X = I⁻  } ion-exchange
1b2 X = Cl⁻ (mixture)  } chiral SFC / ion-exchange
1b2 X = Cl⁻ (pure stereoisomer)

Mixtures of (R)-4-((1R,3S)-6-chloro-3-phenyl-2,3-dihydro-1H-inden-1-yl)-1,2,2-trimethyl-1-((pivaloyloxy)methyl)piperazin-1-ium iodide and (S)-4-((1R,3S)-6-chloro-3-phenyl-2,3-dihydro-1H-inden-1-yl)-1,2,2-trimethyl-1-((pivaloyloxy)methyl)piperazin-1-ium iodide (1a2; X=I⁻ and 1b2; X=I⁻) and (R)-4-((1R,3S)-6-chloro-3-phenyl-2,3-dihydro-1H-inden-1-yl)-1,2,2-trimethyl-1-((pivaloyloxy)methyl)piperazin-1-ium chloride and (S)-4-((1R,3S)-6-chloro-3-phenyl-2,3-dihydro-1H-inden-1-yl)-1,2,2-trimethyl-1-((pivaloyloxy)methyl)piperazin-1-ium chloride (1a2; X=Cl⁻ and 1b2; X=Cl⁻) were prepared in a similar manner as 1a1 and 1b1. The synthesis started from 4-((1R,3S)-6-chloro-3-phenyl-2,3-dihydro-1H-inden-1-yl)-1,2,2-trimethylpiperazine (1; 4.6 g) and iodomethyl pivalate (3b; 6.27 g) in acetonitrile (32 mL) to afford ca. 5 g crude iodide and ca. 4 g HPLC-purified (method 3) mixture of (R)-4-((1R,3S)-6-chloro-3-phenyl-2,3-dihydro-1H-inden-1-yl)-2,2-dimethyl-1-methyl-1-((pivaloyloxy)methyl)piperazin-1-ium chloride and (S)-4-((1R,3S)-6-chloro-3-phenyl-2,3-dihydro-1H-inden-1-yl)-2,2-dimethyl-1-methyl-1-((pivaloyloxy)methyl)piperazin-1-ium chloride (1a2; X=Cl⁻ and 1b2; X=Cl⁻). This mixture was separated by chiral SFC (method 4). The two products were purified as before using methods 11 and 3 to afford two products:

First eluting isomer: 1.00 g of either (R)-4-((1R,3S)-6-chloro-3-phenyl-2,3-dihydro-1H-inden-1-yl)-1,2,2-trimethyl-1-((pivaloyloxy)methyl)piperazin-1-ium chloride (1a2; X=Cl⁻) or (S)-4-((1R,3S)-6-chloro-3-phenyl-2,3-dihydro-1H-inden-1-yl)-1,2,2-trimethyl-1-((pivaloyloxy)methyl)piperazin-1-ium chloride (1b2; X=Cl⁻).

¹H NMR: 400 MHz Methanol-d₄ 7.71 (broad s., 1H), 7.39-7.27 (m, 3H), 7.26-7.19 (m, 1H), 7.18-7.10 (m, 2H), 6.97 (d, J=8.4 Hz, 1H), 5.70-5.57 (m, 1H), 5.52 (d, J=8.8 Hz, 1H), 4.93 (broad s., 1H), 4.69 (t, J=7.6 Hz, 1H), 3.85 (broad s., 2H), 3.50-3.31 (m, 4H), 3.16 (s, 3H), 3.05-2.92 (m, 1H), 2.42-2.28 (m, 1H), 1.71 (broad s, 6H), 1.31 (s, 9H).

LC/MS (method 12): retention time 3.12 min, 98.5% UV purity (220 nm), m/z mass observed 469.2.

SFC (method 5): retention time 1.91 min, >99% UV purity (220 nm).

Second eluting isomer: 0.80 g of either (S)-4-((1R,3S)-6-chloro-3-phenyl-2,3-dihydro-1H-inden-1-yl)-1,2,2-trimethyl-1-((pivaloyloxy)methyl)piperazin-1-ium chloride (1b2; X=Cl⁻) or (R)-4-((1R,3S)-6-chloro-3-phenyl-2,3-dihydro-1H-inden-1-yl)-1,2,2-trimethyl-1-((pivaloyloxy)methyl)piperazin-1-ium chloride (1a2; X=Cl⁻).

¹H NMR: 400 MHz Methanol-d₄ 7.69 (broad s., 1H), 7.37-7.26 (m, 3H), 7.26-7.18 (m, 1H), 7.14 (d, J=7.2 Hz, 2H), 6.96 (d, J=8.4 Hz, 1H), 5.58-5.40 (m, 2H), 4.90 (broad s., 1H), 4.65 (broad s., 1H), 3.94 (broad s., 1H), 3.70 (d, J=14.0 Hz, 1H), 3.36 (broad s., 3H), 3.22 (broad s., 3H), 3.16-2.90 (m, 2H), 2.39-2.25 (m, 1H), 1.79-1.56 (m, 6H), 1.31 (s, 9H).

LC/MS (method 7): retention time 2.72 min, 97% UV purity (220 nm), m/z mass observed 469.2.

SFC (method 5): retention time 2.36 min, >96% UV purity (220 nm).

Example 7: Preparation of Pivaloyloxymethyl 2a and 2b

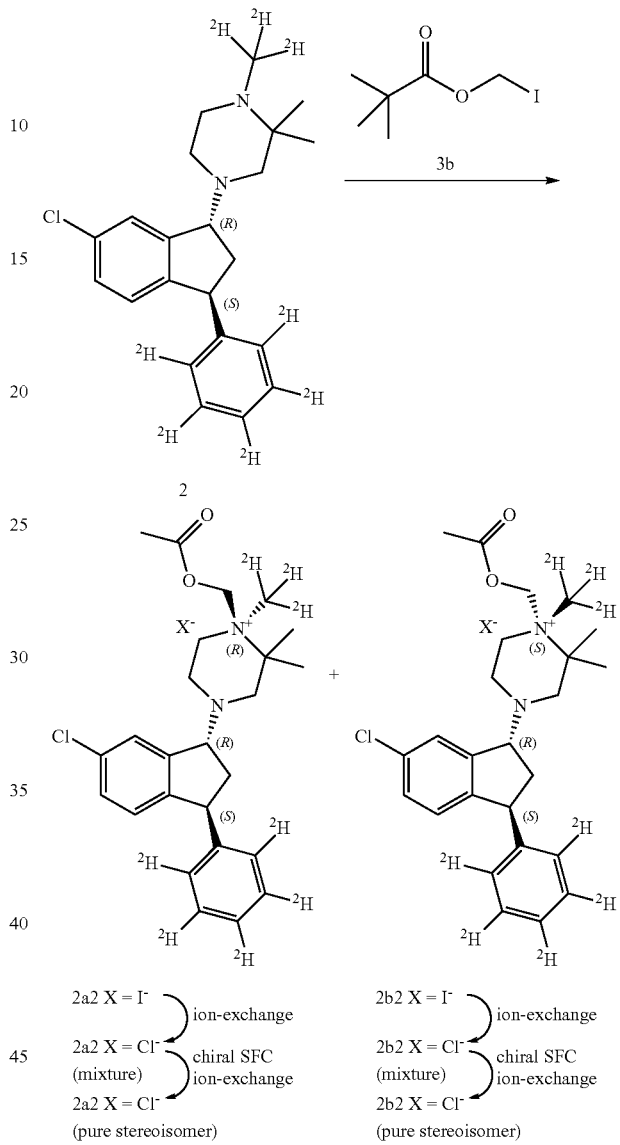

Mixtures of (R)-4-((1R,3S)-6-chloro-3-(phenyl-d₅)-2,3-dihydro-1H-inden-1-yl)-2,2-dimethyl-1-(methyl-d₃)-1-((pivaloyloxy)methyl)piperazin-1-ium iodide and (S)-4-((1R,3S)-6-chloro-3-(phenyl-d₅)-2,3-dihydro-1H-inden-1-yl)-2,2-dimethyl-1-(methyl-d₃)-1-((pivaloyloxy)methyl)piperazin-1-ium iodide (2a2; X=I⁻ and 2b2; X=I⁻) and (R)-4-((1R,3S)-6-chloro-3-(phenyl-d₅)-2,3-dihydro-1H-inden-1-yl)-2,2-dimethyl-1-(methyl-d₃)-1-((pivaloyloxy)methyl)piperazin-1-ium chloride and (S)-4-((1R,3S)-6-chloro-3-(phenyl-d₅)-2,3-dihydro-1H-inden-1-yl)-2,2-dimethyl-1-(methyl-d₃)-1-((pivaloyloxy)methyl)piperazin-1-ium chloride (2a2; X=Cl⁻ and 2b2; X=Cl⁻) were prepared in a similar manner as 1a1 and 1b1. The synthesis started from 4-((1R,3S)-6-chloro-3-(phenyl-d₅)-2,3-dihydro-1H-inden-1-yl)-2,2-dimethyl-1-(methyl-d₃)piperazine (2; 6.00 g) and iodomethyl pivalate (3b; 8.00 g) in acetonitrile (42 mL) to afford ca. 5 g crude iodide and ca. 4 g HPLC-purified (method 3) mixture of (R)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium chloride and (S)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium chloride (2a2; X=Cl⁻ and 2b2; X=Cl⁻). This mixture was separated by chiral SFC (method 6). The two products were purified as before using methods 11 and 3 to afford two products:

First eluting isomer: 1.00 g of either (R)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium chloride (2a2; X=Cl⁻) or (S)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium chloride (2b2; X=Cl⁻).

¹H NMR: 400 MHz Methanol-$d_4$ 7.71 (broad s, 1H), 7.36 (dd, J=2.0, 8.1 Hz, 1H), 6.97 (d, J=7.9 Hz, 1H), 5.61 (broad s, 1H), 5.52 (d, J=8.8 Hz, 1H), 5.00-4.89 (m, 1H), 4.68 (s, 1H), 3.85 (broad s, 2H), 3.54-3.31 (m, 3H), 3.28-3.16 (m, 1H), 2.99 (broad dd, J=10.3, 13.8 Hz, 1H), 2.43-2.28 (m, 1H), 1.71 (broad s, 6H), 1.32 (s, 9H).

LC/MS (method 7): retention time 2.72 min, 98.9% UV purity (220 nm), m/z mass observed 477.3.

SFC (method 5): retention time 1.79 min, >99% UV purity (220 nm).

Second eluting isomer: 0.72 g of either (S)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium chloride (2b2; X=Cl⁻) or (R)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium chloride (2a2; X=Cl⁻).

¹H NMR: 400 MHz Methanol-$d_4$ 7.44 (d, J=2.2 Hz, 1H), 7.25 (dd, J=2.0, 8.1 Hz, 1H), 6.94 (d, J=8.3 Hz, 1H), 5.52-5.45 (m, 1H), 5.45-5.39 (m, 1H), 4.58 (dd, J=3.9, 7.9 Hz, 1H), 4.46 (t, J=7.7 Hz, 1H), 3.74 (broad s, 1H), 3.53 (broad d, J=12.7 Hz, 1H), 3.09-2.74 (m, 4H), 2.63 (broad s, 1H), 2.21-2.04 (m, 1H), 1.69-1.48 (m, 6H), 1.38-1.24 (m, 9H).

LC/MS (method 7): retention time 2.72 min, 97.6% UV purity (220 nm), m/z mass observed 477.3.

SFC (method 5): retention time 2.1 min, >97% UV purity (220 nm).

Example 8: Preparation of Dodecanoyloxymethyl 1a and 1b

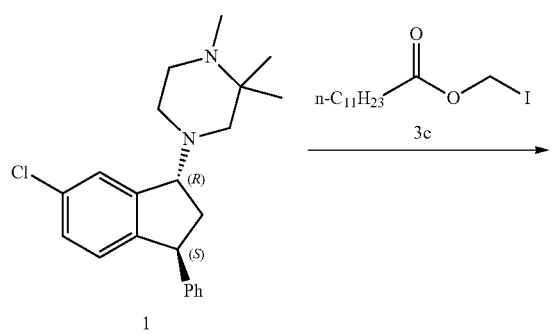

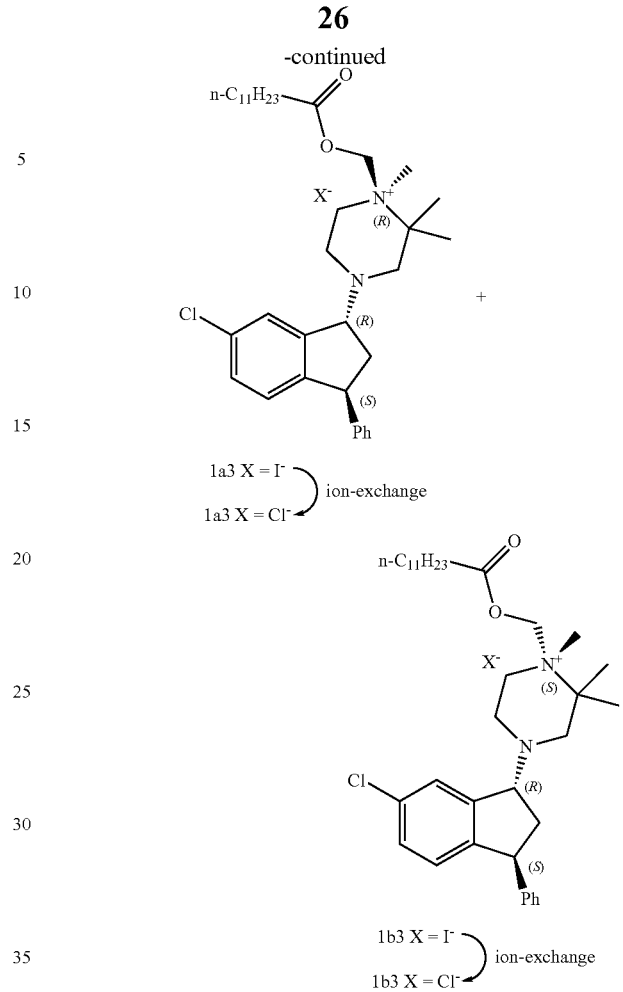

Mixtures of (R)-4-((1R,3S)-6-chloro-3-phenyl-2,3-dihydro-1H-inden-1-yl)-1-((dodecanoyloxy)methyl)-1,2,2-trimethylpiperazin-1-ium iodide and (S)-4-((1R,3S)-6-chloro-3-phenyl-2,3-dihydro-1H-inden-1-yl)-1-((dodecanoyloxy)methyl)-1,2,2-trimethylpiperazin-1-ium iodide (1a3; X=I⁻ and 1b3; X=I⁻) and (R)-4-((1R,3S)-6-chloro-3-phenyl-2,3-dihydro-1H-inden-1-yl)-1-((dodecanoyloxy)methyl)-1,2,2-trimethylpiperazin-1-ium chloride and (S)-4-((1R,3S)-6-chloro-3-phenyl-2,3-dihydro-1H-inden-1-yl)-1-((dodecanoyloxy)methyl)-1,2,2-trimethylpiperazin-1-ium chloride (1a3; X=Cl⁻ and 1b3; X=Cl⁻) were prepared in a similar manner as 1a1 and 1b1. The synthesis started from 4-((1R,3S)-6-chloro-3-phenyl-2,3-dihydro-1H-inden-1-yl)-1,2,2-trimethylpiperazine (1; 7.00 g) and iodomethyl dodecanoate (3c; 16.8 g) in acetonitrile (49 mL) to afford afford ca. 5.5 g crude iodide. This material was purified by reverse-phase column chromatography (method 18) followed by ion-exchange (method 11) to afford 3.2 g of a mixture of (R)-4-((1R,3S)-6-chloro-3-phenyl-2,3-dihydro-1H-inden-1-yl)-1-((dodecanoyloxy)methyl)-1,2,2-trimethylpiperazin-1-ium chloride and (S)-4-((1R,3S)-6-chloro-3-phenyl-2,3-dihydro-1H-inden-1-yl)-1-((dodecanoyloxy)methyl)-1,2,2-trimethylpiperazin-1-ium chloride (1a3; X=Cl⁻ and 1b3; X=Cl⁻).

¹H NMR: 400 MHz Methanol-d₄ 7.45 (s, 1H), 7.31-7.23 (m, 3H), 7.23-7.17 (m, 1H), 7.13-7.07 (m, 2H), 6.94 (d, J=8.3 Hz, 1H), 5.52 (broad s, 1H), 5.40 (dd, J=3.9, 8.8 Hz, 1H), 4.64-4.55 (m, 1H), 4.47 (broad t, J=7.2 Hz, 1H), 3.81-3.64 (m, 1H), 3.56 (broad d, J=14.5 Hz, 1H), 3.11 (d, J=7.5 Hz, 3H), 3.04-2.91 (m, 2H), 2.86-2.75 (m, 2H), 2.57 (dt, J=1.8, 7.5 Hz, 2H), 2.19-2.06 (m, 1H), 1.71-1.56 (m, 8H), 1.29 (broad s, 17H), 0.93-0.84 (m, 3H).

LC/MS (method 13): retention time 2.66 min, 99.3% UV purity (220 nm), m/z mass observed 567.3.

Example 9: Preparation of Dodecanoyloxymethyl 2a and 2b

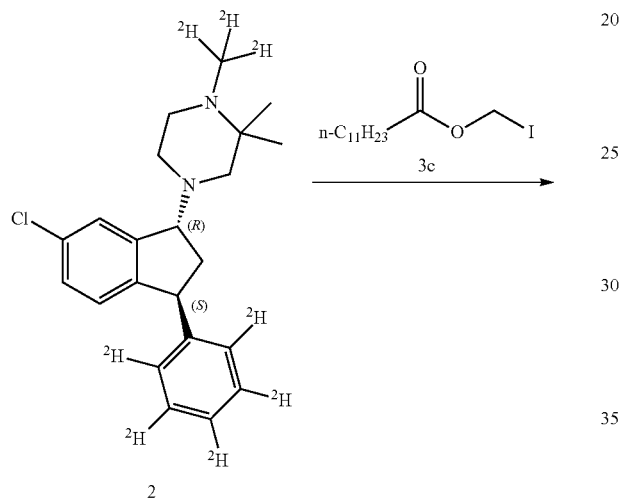

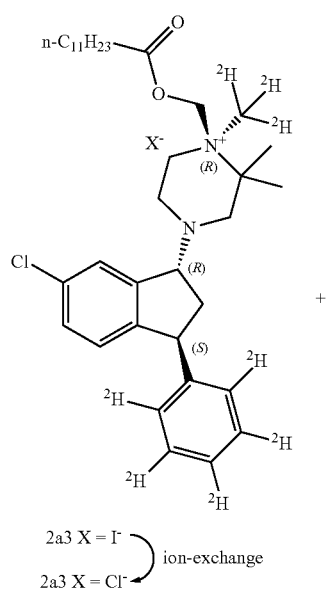

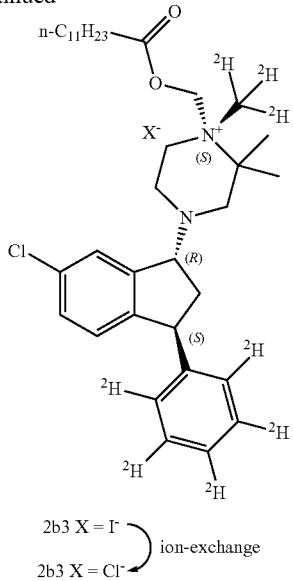

Mixtures of (R)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃)piperazin-1-ium iodide and (S)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃) piperazin-1-ium iodide (2a3; X=I⁻ and 2b3; X=I⁻) and (R)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃)piperazin-1-ium chloride and (S)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃) piperazin-1-ium chloride (2a3; X=Cl⁻ and 2b3; X=Cl⁻) were prepared in a similar manner as 1a3 and 1b3. The synthesis started from 4-((1R,3S)-6-chloro-3-(phenyl-d₅)-2,3-dihydro-1H-inden-1-yl)-2,2-dimethyl-1-(methyl-d₃)piperazine (2; 5.60 g) and iodomethyl dodecanoate (3c; 10.5 g) in acetonitrile (39 mL) to afford ca. 5 g crude iodide and 3.1 g of a mixture of (R)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃)piperazin-1-ium chloride and (S)-4-((1R,3S)-6-chloro-3-(phenyl-d₅)-2,3-dihydro-1H-inden-1-yl)-1-((dodecanoyloxy)methyl)-2,2-dimethyl-1-(methyl-d₃) piperazin-1-ium chloride (2a3; X=Cl⁻ and 2b3; X=Cl⁻).

¹H NMR: 400 MHz Methanol-d₄ 7.49 (broad s, 1H), 7.27 (d, J=8.3 Hz, 1H), 6.94 (d, J=8.3 Hz, 1H), 5.52 (broad s, 1H), 5.46-5.36 (m, 1H), 4.69-4.58 (m, 1H), 4.50 (broad t, J=7.5 Hz, 1H), 3.86-3.66 (m, 1H), 3.61 (broad s, 1H), 3.16-2.79 (m, 4H), 2.57 (dt, J=1.3, 7.5 Hz, 2H), 2.23-2.07 (m, 1H), 1.76-1.51 (m, 8H), 1.47-1.19 (m, 17H), 0.95-0.83 (m, 3H).

LC/MS (method 13): retention time 2.68 min, 98.9% UV purity (220 nm), m/z mass observed 575.4.

Example 10: Preparation of Cyclohexylacetoxymethyl 1a and 1b

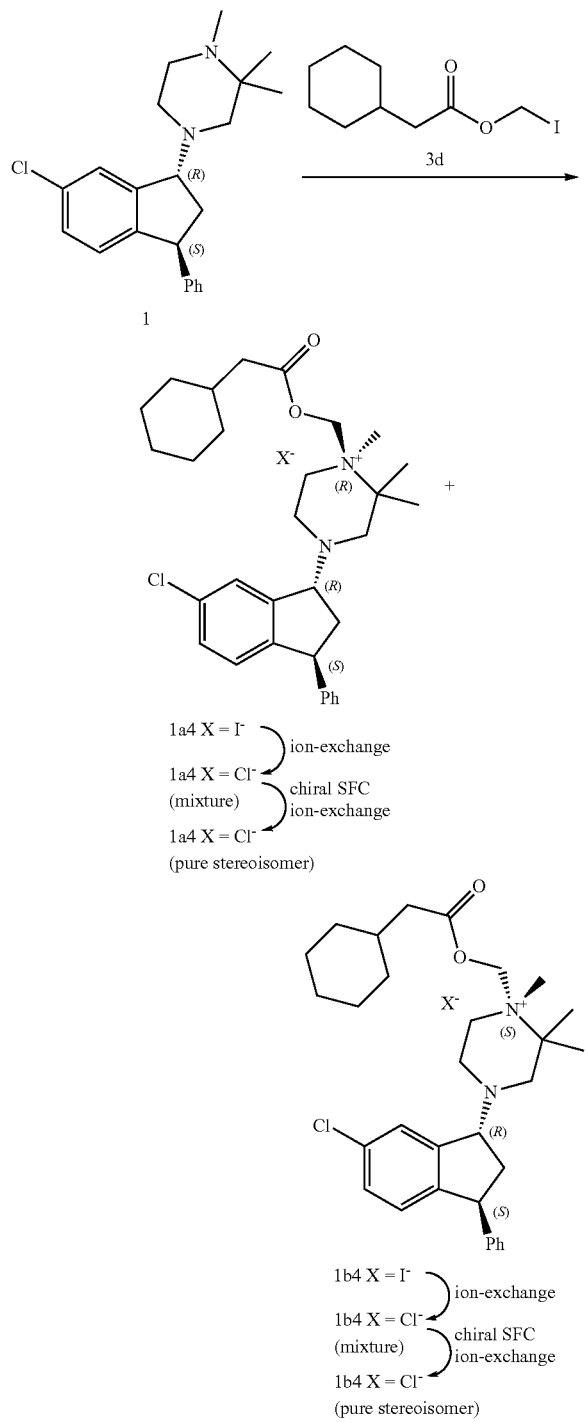

Mixtures of (R)-4-((1R,3S)-6-chloro-3-phenyl-2,3-dihydro-1H-inden-1-yl)-1-((2-cyclohexylacetoxy)methyl)-1,2,2-trimethylpiperazin-1-ium iodide and (S)-4-((1R,3S)-6-chloro-3-phenyl-2,3-dihydro-1H-inden-1-yl)-1-((2-cyclohexylacetoxy)methyl)-1,2,2-trimethylpiperazin-1-ium iodide (1a4; X=I⁻ and 1b4; X=I⁻) and (R)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride and (S)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride (1a4; X=Cl⁻ and 1b4; X=Cl⁻) were prepared in a similar manner as 1a1 and 1b1. The synthesis started from 4-((1R,3S)-6-chloro-3-phenyl-2,3-dihydro-1H-inden-1-yl)-1,2,2-trimethylpiperazine (1, 6.00 g) and iodomethyl 2-cyclohexylacetate (3d; 11.9 g) in acetonitrile (42 mL) to afford ca. 8 g crude iodide and 3.2 g HPLC-purified mixture (method 8) of (R)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride and (S)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride (1a4; X=Cl⁻ and 1b4; X=Cl⁻). This mixture of was separated by chiral SFC (method 9). The two products were purified as before using methods 11 and 8 to afford two products:

First eluting isomer: 1.00 g of either (R)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride (1a4; X=Cl⁻) or (S)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride (1b4; X=Cl⁻).

$^1$H NMR: 400 MHz Methanol-$d_4$ 7.57 (broad s, 1H), 7.32-7.26 (m, 3H), 7.25-7.19 (m, 1H), 7.15-7.09 (m, 2H), 6.95 (d, J=8.3 Hz, 1H), 5.56 (broad s, 1H), 5.45 (d, J=8.8 Hz, 1H), 4.74 (broad s, 1H), 4.57 (broad t, J=7.5 Hz, 1H), 3.84-3.60 (m, 2H), 3.27-2.77 (m, 8H), 2.46 (d, J=7.0 Hz, 2H), 2.23 (td, J=7.2, 14.5 Hz, 1H), 1.99-1.47 (m, 12H), 1.39-1.13 (m, 3H), 1.12-0.96 (m, 2H)

LC/MS (method 14): retention time 2.85 min, 97.4% UV purity (220 nm), m/z mass observed 509.3.

SFC (method 10): retention time 2.45 min, >99% UV purity (220 nm).

Second eluting isomer: 0.33 g of either (S)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride (1b4; X=Cl⁻) or (R)-4-((1R,3S)-6-chloro-3-phenyl-2,3-dihydro-1H-inden-1-yl)-1-((2-cyclohexylacetoxy)methyl)-1,2,2-trimethylpiperazin-1-ium chloride (1a4; X=Cl⁻).

$^1$H NMR: 400 MHz Methanol-$d_4$ 7.51 (s, 1H), 7.33-7.26 (m, 3H), 7.25-7.19 (m, 1H), 7.14-7.09 (m, 2H), 6.96 (d, J=8.8 Hz, 1H), 5.56-5.47 (m, 1H), 5.46-5.39 (m, 1H), 4.72-4.64 (m, 1H), 4.52 (broad t, J=7.7 Hz, 1H), 3.79 (broad s, 1H), 3.62 (broad s, 1H), 3.21-2.77 (m, 8H), 2.46 (d, J=6.8 Hz, 2H), 2.26-2.12 (m, 1H), 1.85-1.55 (m, 12H), 1.43-1.16 (m, 3H), 1.12-0.97 (m, 2H).

LC/MS (method 15): retention time 3.66 min, 97.7% UV purity (220 nm), m/z mass observed 509.2.

SFC (method 10): retention time 6.41 min, >97% UV purity (220 nm).

Example 11: Preparation of Cyclohexylacetoxymethyl 2a and 2b

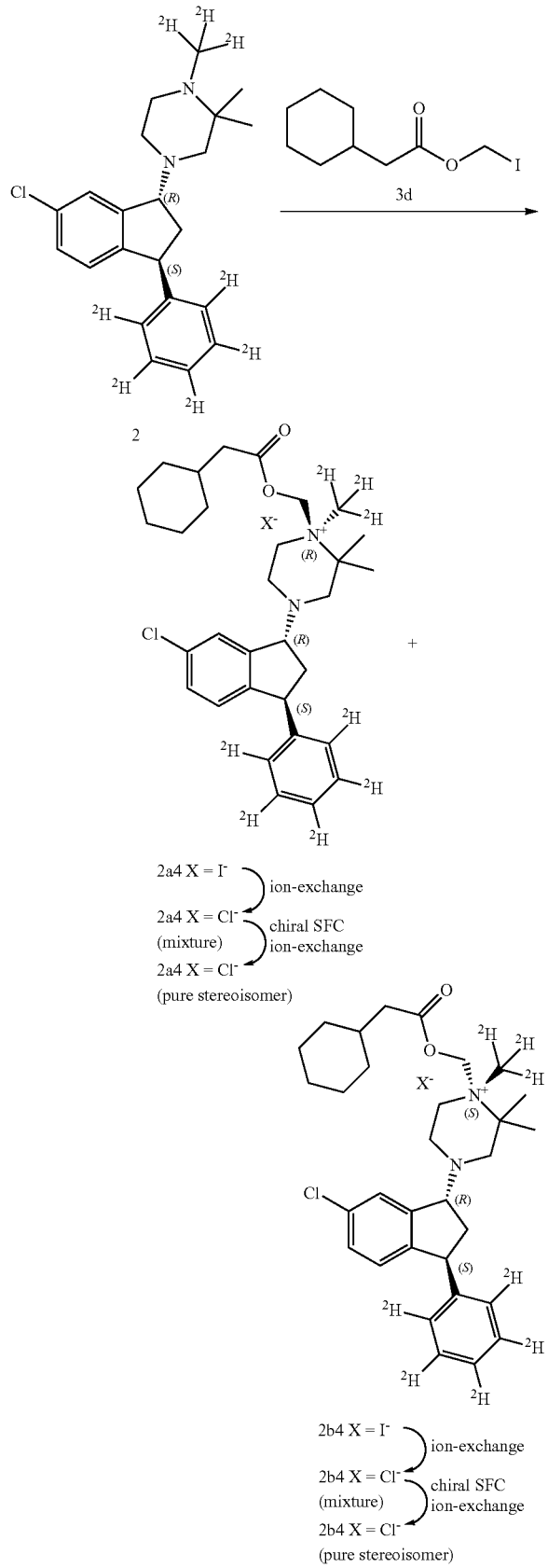

Mixture of (R)-4-((1R,3S)-6-chloro-3-(phenyl-$d_5$)-2,3-dihydro-1H-inden-1-yl)-1-((2-cyclo-hexylacetoxy)methyl)-2,2-dimethyl-1-(methyl-$d_3$)piperazin-1-ium iodide and (S)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium iodide (2a4; X=I$^-$ and 2b4; X=I$^-$) and (R)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium chloride and (S)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium chloride (2a4; X=Cl$^-$ and 2b4; X=Cl$^-$) were prepared in a similar manner as 1a1 and 1b1. The synthesis started from 4-((1R,3S)-6-chloro-3-(phenyl-$d_5$)-2,3-dihydro-1H-inden-1-yl)-2,2-dimethyl-1-(methyl-$d_3$) piperazine (2; 6.00 g) and iodomethyl 2-cyclohexylacetate (3d; 11.7 g) in acetonitrile (42 mL) to afford ca. 7.8 g crude iodide and 6 g HPLC-purified (method 8) mixture of (R)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium chloride and (S)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$) piperazin-1-ium chloride (2a4; X=Cl$^-$ and 2b4; X=Cl$^-$). This mixture was separated by chiral SFC (method 16). The two products were purified as before using methods 11 and 8 to afford two products:

First eluting isomer: 1.10 g of either (R)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium chloride (2a4; X=Cl$^-$) or (S)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$) piperazin-1-ium chloride (2b4; X=Cl$^-$).

$^1$H NMR: 400 MHz Methanol-$d_4$ 7.50 (broad s, 1H), 7.30 (broad d, J=8.2 Hz, 1H), 6.97 (d, J=8.2 Hz, 1H), 5.54 (broad s, 1H), 5.49-5.41 (m, 1H), 4.66 (broad s, 1H), 4.58-4.48 (m, 1H), 3.73 (broad s, 1H), 3.62 (broad s, 1H), 3.21-2.74 (m, 5H), 2.47 (d, J=6.8 Hz, 2H), 2.26-2.12 (m, 1H), 1.92-1.57 (m, 12H), 1.38-1.17 (m, 3H), 1.14-0.98 (m, 2H).

LC/MS (method 14): retention time 2.68 min, 96.6% UV purity (220 nm), m/z mass observed 517.2.

SFC (method 10): retention time 2.33 min, >97% UV purity (220 nm).

Second eluting isomer: 1.10 g of either (S)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium chloride (2b4; X=Cl$^-$) or (R)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$) piperazin-1-ium chloride (2a4; X=Cl$^-$).

$^1$H NMR: 400 MHz Methanol-$d_4$ 7.48 (broad s, 1H), 7.28 (d, J=8.2 Hz, 1H), 6.95 (d, J=8.2 Hz, 1H), 5.49 (broad s, 1H), 5.44-5.38 (m, 1H), 4.64 (broad d, J=4.0 Hz, 1H), 4.49 (broad s, 1H), 3.83-3.70 (m, 1H), 3.58 (broad d, J=13.2 Hz, 1H), 3.16-2.63 (m, 5H), 2.45 (d, J=6.8 Hz, 2H), 2.16 (broad dd, J=6.9, 10.7 Hz, 1H), 1.91-1.51 (m, 12H), 1.43-1.16 (m, 3H), 1.13-0.95 (m, 2H).

LC/MS (method 7): retention time 2.99 min, 99.4% UV purity (220 nm), m/z mass observed 517.3.

SFC (method 10): retention time 4.87 min, >97% UV purity (220 nm).

Example 12: Plasma Stability Assay

Frozen human plasma (stored at −80° C.) was thawed in a water bath followed by centrifugation at 3200×g for 5 min to remove debris. The pH value of the supernatant was then measured and adjusted to 7.4±0.1 by adding 1% phosphoric acid or 1 N sodium hydroxide.

For each test compound, 2 microL of dosing solution (50 microM for test compounds and 100 microM for positive control; propantheline bromide) were spiked into 98 microL of blank plasma to achieve a final concentration of 1 microM test compound and 2 microM positive control.

The test compounds and positive control were incubated in duplicate with human plasma (final DMSO concentration<1%) in a water bath at 37° C. at six different time points (0, 0.5, 1, 2, 4 and 6 hr). At each corresponding time point the incubations were terminated by adding appropriate volume of quenching solution to stop the reaction.

Afterwards, the plasma samples were briefly vortexed and subsequently centrifuged at 3200×g for 20 min. The supernatant was transferred into a 96-well plate and diluted with 200 microL of ultrapure water in the ratio of 1:2 prior to LC-MS/MS analysis. The peak area ratios (PAR) of analyte/internal standard was used to semi-quantitatively determine the concentration of test compounds and control compound. The percentage of test compound remaining at the individual time points relative to the 0 minute sample was reported.

In the determination of in vitro elimination constant, ke, of the parent drug and controls, the analyte/internal standard peak area ratios were converted to percentage remaining with the following equation:

$$\% \text{ Remaining} = \frac{\text{Peak area ratio of analyte to internal standard at each time point}}{\text{Peak area ratio of analyte to internal standard at } t = 0} \times 100\%$$

The percentage formation of metabolite was calculated by the analyte/internal standard peak area ratios versus T0 (absolute) of metabolite drug and converted to percentage.

The half-life (T½) of parent drug and control compounds were calculated from a log linear plot of analyte/internal standard peak area ratios versus time (T½=0.693/ke).

Compounds 1a2, 1b2, 2a2, and 2b2 were incubated in human plasma as described above and half-lives of 0.5-1.5 h were determined with the formation of 15-35% of 4-((1R,3S)-6-chloro-3-phenyl-2,3-dihydro-1H-inden-1-yl)-1,2,2-trimethylpiperazine and 4-((1R,3S)-6-chloro-3-(phenyl-d$_5$)-2,3-dihydro-1H-inden-1-yl)-2,2-dimethyl-1-(methyl-d$_3$)piperazine, respectively.

The invention claimed is:
1. A prodrug of 4-((1R,3S)-6-chloro-3-phenyl-2,3-dihydro-1H-inden-1-yl)-1,2,2-trimethylpiperazine in the form of 1a or 1b or 4-((1R,3S)-6-chloro-3-(phenyl-d$_5$)-2,3-dihydro-1H-inden-1-yl)-2,2-dimethyl-1-(methyl-d$_3$)piperazine in the form of 2a and 2b

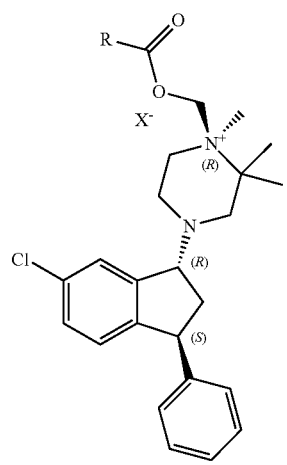

1a

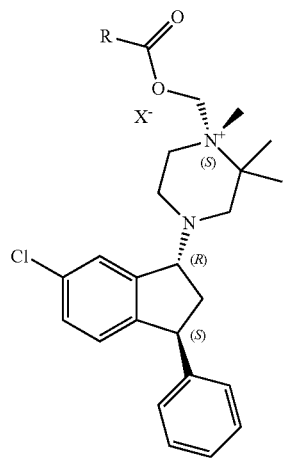

1b

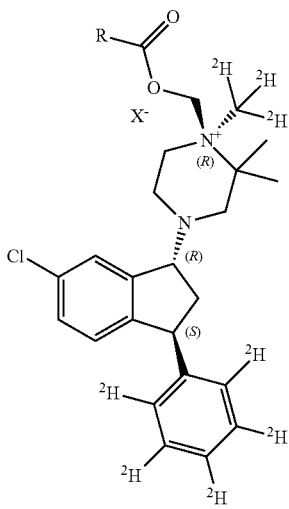

2a

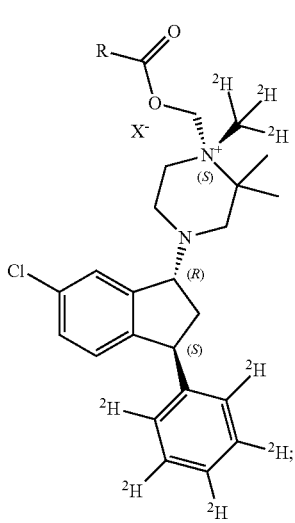

wherein X⁻ is a counter ion selected from the group consisting of halide anion, optionally fluorinated $C_1$-$C_{10}$ sulfonate, and optionally fluorinated linear or branched $C_1$-$C_{11}$ carboxylate, and wherein R is selected from the group consisting of linear or branched $C_1$-$C_{11}$ alkyl and $C_3$-$C_{10}$ cycloalkyl;

or a pharmaceutically acceptable salt thereof.

2. The prodrug according to claim 1, wherein R is linear or branched $C_1$-$C_{11}$ alkyl, or a pharmaceutically acceptable salt thereof.

3. The prodrug according to claim 1, wherein R is selected from the group consisting of methyl, tertbutyl, n-undecane and cyclohexylmethyl, or a pharmaceutically acceptable salt thereof.

4. The prodrug, or a pharmaceutically acceptable salt thereof, according to claim 1, wherein the pharmaceutically acceptable salt is selected from the group consisting of salts formed from hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin and sulfonic acids.

5. The prodrug according to claim 1 selected from the group consisting of (R)-1-(acetoxymethyl)-4-((1R,3S)-6-chloro-3-phenyl-2,3-dihydro-1H-inden-1-yl)-1,2,2-trimethylpiperazin-1-ium, (S)-1-(acetoxymethyl)-4-((1R,3S)-6-chloro-3-phenyl-2,3-dihydro-1H-inden-1-yl)-1,2,2-trimethylpiperazin-1-ium, (R)-1-(acetoxymethyl)-4-((1R,3S)-6-chloro-3-(phenyl-$d_5$)-2,3-dihydro-1H-inden-1-yl)-2,2-dimethyl-1-(methyl-$d_3$)piperazin-1-ium, (S)-1-(acetoxymethyl)-4-((1R,3S)-6-chloro-3-(phenyl-$d_5$)-2,3-dihydro-1H-inden-1-yl)-2,2-dimethyl-1-(methyl-$d_3$)piperazin-1-ium, (R)-4-((1R,3S)-6-chloro-3-phenyl-2,3-dihydro-1H-inden-1-yl)-2,2-dimethyl-1-methyl-1-((pivaloyloxy)methyl)piperazin-1-ium, (S)-4-((1R,3S)-6-chloro-3-phenyl-2,3-dihydro-1H-inden-1-yl)-2,2-dimethyl-1-methyl-1-((pivaloyloxy)methyl)piperazin-1-ium, (R)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium, (S)-4-((1R,3S)-6-chloro-3-(phenyl-$d_5$)-2,3-dihydro-1H-inden-1-yl)-2,2-dimethyl-1-(methyl-$d_3$)-1-((pivaloyloxy)methyl)piperazin-1-ium, (R)-4-((1R,3S)-6-chloro-3-phenyl-2,3-dihydro-1H-inden-1-yl)-1-((dodecanoyloxy)methyl)-1,2,2-trimethylpiperazin-1-ium, (S)-4-((1R,3S)-6-chloro-3-phenyl-2,3-dihydro-1H-inden-1-yl)-1-((dodecanoyloxy)methyl)-1,2,2-trimethylpiperazin-1-ium, (R)-4-((1R,3S)-6-chloro-3-(phenyl-$d_5$)-2,3-dihydro-1H-inden-1-yl)-1-((dodecanoyloxy)methyl)-2,2-dimethyl-1-(methyl-$d_3$)piperazin-1-ium, (S)-4-((1R,3S)-6-chloro-3-(phenyl-$d_5$)-2,3-dihydro-1H-inden-1-yl)-1-((dodecanoyloxy)methyl)-2,2-dimethyl-1-(methyl-$d_3$)piperazin-1-ium, (R)-4-((1R,3S)-6-chloro-3-phenyl-2,3-dihydro-1H-inden-1-yl)-1-((2-cyclohexylacetoxy)methyl)-1,2,2-trimethylpiperazin-1-ium, (S)-4-((1R,3S)-6-chloro-3-phenyl-2,3-dihydro-1H-inden-1-yl)-1-((2-cyclohexylacetoxy)methyl)-1,2,2-trimethylpiperazin-1-ium, (R)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium, and (S)-4-((1R,3S)-6-chloro-3-(phenyl-$d_5$)-2,3-dihydro-1H-inden-1-yl)-1-((2-cyclohexylacetoxy)methyl)-2,2-dimethyl-1-(methyl-$d_3$)piperazin-1-ium, each of which is combined with a counter ion selected from the group consisting of halide anion, optionally fluorinated $C_1$-$C_{10}$ sulfonate, and optionally fluorinated linear or branched $C_1$-$C_{11}$ carboxylate; or a pharmaceutically acceptable salt thereof.

6. A pharmaceutical composition comprising any of the prodrugs of claim 1, or a pharmaceutically acceptable salt thereof, and one or more pharmaceutically acceptable excipients.

7. The prodrug according to claim 1, wherein R is $C_3$-$C_{10}$ cycloalkyl, or a pharmaceutically acceptable salt thereof.

8. The prodrug, or a pharmaceutically acceptable salt thereof, according to claim 1, wherein the pharmaceutically acceptable salt is selected from the group consisting of salts formed from methanesulfonic acid, ethanesulfonic acid, toluenesulfonic acid and benzenesulfonic acid.

9. The prodrug, or a pharmaceutically acceptable salt thereof, according to claim 2, wherein the pharmaceutically acceptable salt is selected from the group consisting of salts formed from hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin and sulfonic acids.

10. The prodrug, or a pharmaceutically acceptable salt thereof, according to claim 3, wherein the pharmaceutically acceptable salt is selected from the group consisting of salts formed from hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin and sulfonic acids.

11. The prodrug, or a pharmaceutically acceptable salt thereof, according to claim 7, wherein the pharmaceutically acceptable salt is selected from the group consisting of salts formed from hydrochloride acid, hydrobromide acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, saccharin and sulfonic acids.

12. The prodrug, or a pharmaceutically acceptable salt thereof, according to claim 5, wherein the counter ion is selected from the group consisting of chloride, bromide and iodide.

13. The prodrug, or a pharmaceutically acceptable salt thereof, according to claim 5, wherein the counter ion is selected from the group consisting of mesylate, tosylate, trifluoromethanesulfonate, and nonafluorobutanesulfonate.

14. The prodrug, or a pharmaceutically acceptable salt thereof, according to claim 5, wherein the counter ion is trifluoroacetate.

15. The prodrug, or a pharmaceutically acceptable salt thereof, according to claim 1, wherein the counter ion is selected from the group consisting of chloride, bromide, iodide, mesylate, tosylate, trifluoromethanesulfonate, nonafluorobutanesulfonate, and trifluoroacetate.

* * * * *